United States Patent
Costa et al.

(10) Patent No.: US 11,683,577 B2
(45) Date of Patent: *Jun. 20, 2023

(54) SYSTEMS AND METHODS FOR REGISTERING HEADSET SYSTEM

(71) Applicant: NovaSignal Corp., Los Angeles, CA (US)

(72) Inventors: Michael Costa, Los Angeles, CA (US); Trevor Dunlop, Los Angeles, CA (US); Roman Flores, II, Los Angeles, CA (US); Matthew Hutter, Los Angeles, CA (US); Michael O'Brien, Los Angeles, CA (US); Ilyas Patanam, Los Angeles, CA (US); Mina Ranjbaran, Los Angeles, CA (US); Gerard Salinas, Los Angeles, CA (US); Fabien Scalzo, Los Angeles, CA (US); Lane Stith, Los Angeles, CA (US); Matthew Sylvester, Los Angeles, CA (US); Justin White, Los Angeles, CA (US); Jan Zwierstra, Los Angeles, CA (US)

(73) Assignee: NovaSignal Corp., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/537,060

(22) Filed: Nov. 29, 2021

(65) Prior Publication Data

US 2022/0224827 A1 Jul. 14, 2022

Related U.S. Application Data

(63) Continuation of application No. 16/837,651, filed on Apr. 1, 2020, now Pat. No. 11,190,677, which is a
(Continued)

(51) Int. Cl.
H04N 23/61 (2023.01)
A61B 8/00 (2006.01)
(Continued)

(52) U.S. Cl.
CPC .......... *H04N 23/61* (2023.01); *A61B 8/4209* (2013.01); *A61B 8/4245* (2013.01); *H04N 1/00* (2013.01);
(Continued)

(58) Field of Classification Search
CPC ...... A61B 8/4209; A61B 8/4245; H04N 1/00; H04N 23/54; H04N 23/61; H04N 23/695; H04N 1/409292; H04N 1/4092
See application file for complete search history.

(56) References Cited

U.S. PATENT DOCUMENTS 9,171,379 B2  10/2015  Mack et al.
11,452,887 B2 *  9/2022  Kim ..................... A61B 90/18
(Continued)

FOREIGN PATENT DOCUMENTS

| WO | WO-2010/067267 A1 | 6/2010 |       |
|----|-------------------|--------|-------|
| WO | WO-2018/169235 A1 | 9/2018 |       |
| WO | WO-2018169235 A1 * | 9/2018 | ............... A61B 8/00 |

OTHER PUBLICATIONS

Final Office Action dated Jul. 30, 2019, from U.S. Appl. No. 16/132,068.
(Continued)

*Primary Examiner* — Maria E Vazquez Colon
(74) *Attorney, Agent, or Firm* — Foley & Lardner LLP

(57) ABSTRACT

Arrangements described herein relate to systems, apparatuses, and methods for a headset system that includes a transducer, a camera configured to capture image data of a subject, and a controller configured to detect one or more fiducial markers placed on the subject using the captured
(Continued)

image data, and register the transducer with respect to the subject based on the detected fiducial markers.

20 Claims, 15 Drawing Sheets

Related U.S. Application Data continuation of application No. 16/132,068, filed on Sep. 14, 2018, now Pat. No. 10,616,473.

(60) Provisional application No. 62/558,804, filed on Sep. 14, 2017.

(51) Int. Cl.
  *H04N 1/00* (2006.01)
  *H04N 23/54* (2023.01)
  *H04N 23/695* (2023.01)
  *H04N 1/409* (2006.01)

(52) U.S. Cl.
  CPC ........... *H04N 23/54* (2023.01); *H04N 23/695* (2023.01); *H04N 1/4092* (2013.01)

(56) References Cited

U.S. PATENT DOCUMENTS

| 2004/0028258 | A1 | 2/2004 | Naimark et al. | |
|---|---|---|---|---|
| 2009/0129677 | A1 | 5/2009 | Takemoto | |
| 2009/0161827 | A1 | 6/2009 | Gertner et al. | |
| 2013/0237811 | A1 | 9/2013 | Mihailescu et al. | |
| 2013/0245429 | A1 | 9/2013 | Zhang et al. | |
| 2014/0100693 | A1 | 4/2014 | Fong et al. | |
| 2015/0085072 | A1 | 3/2015 | Yan et al. | |
| 2015/0294130 | A1 | 10/2015 | Stein | |
| 2016/0030001 | A1* | 2/2016 | Stein | A61B 8/06 600/431 |
| 2017/0065835 | A1* | 3/2017 | Park | A61B 6/501 |
| 2017/0188992 | A1* | 7/2017 | O'Brien | A61B 8/488 |
| 2018/0296093 | A1* | 10/2018 | Loh | A61B 8/4209 |
| 2019/0184204 | A1* | 6/2019 | Ramamurthy | A61N 7/00 |

OTHER PUBLICATIONS

International Preliminary Report on Patentability dated Mar. 26, 2020, from application No. PCT/US2018/051207.

International Search Report and Written Opinion dated Dec. 4, 2018, from application No. PCT/US2018/051207.

Non-Final Office Action dated Jan. 25, 2019, from U.S. Appl. No. 16/132,068.

Notice of Allowance dated Nov. 27, 2019, from U.S. Appl. No. 16/132,068.

Peter Lightbody et al, "A versatile high-performance visual fiducial marker detection system with scalable identity encoding", Applied Computing, ACM, 2 Penn Plaza, Suite 701 New York NY 10121-0701 USA, Apr. 3, 2017 (Apr. 3, 2017), pp. 276-282, XP058337320, DOI: 10.1145/3019612.3019709, ISBN: 978-1-4503-4486-9.

U.S. Notice of Allowance dated Aug. 2, 2021, from U.S. Appl. No. 16/837,651.

* cited by examiner

500a

SYSTEMS AND METHODS FOR REGISTERING HEADSET SYSTEM

CROSS-REFERENCE TO RELATED PATENT APPLICATIONS

This application is a continuation of U.S. application Ser. No. 16/837,651, filed Apr. 1, 2020, which is a continuation of U.S. application Ser. No. 16/132,068, filed Sep. 14, 2018, now U.S. Pat. No. 10,616,473, granted Apr. 7, 2020, which claims priority from Provisional U.S. Application No. 62/558,804, filed Sep. 14, 2017, which is incorporated herein by reference in its entirety.

BACKGROUND

Performance of a device (e.g., optical devices, surgical devices, scanning devices, medical diagnostic devices, automated Transcranial Doppler devices, and so on) that is incorporated in a headset system is optimized based on the device's positioning with respect to a subject's head. Initial registration (e.g., alignment) of the device with respect to particular areas of the subject's head is important for the device to operate effectively during its operation. In addition, a technician of the headset system performing manual registration of the device may introduce human errors such that performance of the device during operation is adversely affected. In addition, a technician that is highly skilled may be needed to properly register the device, which may impede efficient and timely administration of health care. As such, it is desirable that a headset system including a device can automatically register the device with respect to a subject's head, with minimal required human intervention.

SUMMARY

According to various arrangements, provided are systems and methods that provide automated registration of a headset system with respect to a subject. In some arrangements, automated registration minimizes or eliminates the need for a human technician to operate the headset system, which can minimize human error in operating the system and can result in faster and more efficient execution of operation of the headset system.

In some arrangements, a headset system, includes a transducer, a camera configured to capture image data of a subject, and a controller configured to detect one or more fiducial markers placed on the subject using the captured image data, and register the transducer with respect to the subject based on the detected fiducial markers.

In some arrangements, the transducer is an ultrasound transducer.

In some arrangements, the headset system further includes robotics configured to position the transducer relative to the subject. The controller is configured to register the transducer by positioning the transducer for operation of the transducer on the subject and restricting a workspace of the transducer to one or more boundaries during the operation of the transducer.

In some arrangements, the image data captures the one or more fiducial markers disposed on the subject.

In some arrangements, each of the one or more fiducial markers has retroreflective material capable of reflecting light.

In some arrangements, each of the one or more fiducial markers has a boundary made from a material that reflects less light as compared to the retroreflective material.

In some arrangements, each of the one or more fiducial markers has a fixed size, shape, and design.

In some arrangements, the controller is configured to analyze the captured image data by generating one or more binary images from the image data.

In some arrangements, at least one of the one or more binary images is a threshold-based binary image, and the controller generates the threshold-based binary image by setting a value of each pixel of the image data above a predetermined threshold to be a first value and setting a value of each pixel of the image data below the predetermined threshold to be a second value.

In some arrangements, at least one of the one or more binary images is an edge detection-based binary image.

In some arrangements, the controller is configured to detect contours in the one or more binary images, and select fiducial contours from the detected contours, the fiducial contours being contours of the fiducial markers disposed on the subject while the image data is captured.

In some arrangements, each of the contours having an area-to-perimeter ratio different from an area-to-perimeter ratio of a perfect circle is rejected.

In some arrangements, each of the contours having an area outside of a predetermined range of values is rejected.

In some arrangements, the one or more binary images includes a threshold-based binary image and an edge detection-based binary image. At least one of the detected contours is present in both the threshold-based binary image and the edge detection-based binary image. The at least one of the detected contours is selected to be the fiducial contours.

In some arrangements, the controller is configured to determine a location of each of the fiducial markers based on optical parameters of the camera and a predetermined size of each of the fiducial markers.

In some arrangements, the controller is configured to determine that the location of each of the fiducial markers falls within a range.

In some arrangements, the controller is configured to analyze the captured image data by determining, based on the captured image data, camera coordinates of the one or more fiducial markers placed on the subject, and transforming the camera coordinates into robot coordinates. The controller is configured to register the transducer based on the robot coordinates.

In some arrangements, the controller is configured to determine an allowable robot workspace based on the detected one or more fiducial markers, and determining a path of scanning of the transducer based on the allowable robot workspace.

In some arrangements, the one or more fiducial markers include two fiducial markers, and the controller is configured to detect the one or more fiducial markers by identifying candidate regions using the image data, sorting the candidate regions into candidate region pairs, and determining features for each of the candidate region pairs.

In some arrangements, the controller is configured to detect the one or more fiducial markers by determining a probability that each of the candidate region pairs corresponds to the two fiducials, and selecting one of the candidate region pairs having the highest probability of being the two fiducials.

In some arrangements, the candidate regions are identified by a Maximally Stable Extremal Regions (MSER) algorithm, and the image data includes two images of a lateral side of the subject from different perspectives.

In some arrangements, the features include location, size, eccentricity, image intensity, and local texture of each candidate region in each of the candidate region pairs.

In some arrangements, the features include spatial relationship between candidate regions in each of the candidate region pairs.

In some arrangements, the headset system further includes a device. The device includes a body, the transducer housed by the body, and the camera housed by the body. The camera is configured to move relative to the body to capture image data of the subject.

In some arrangements, the camera is configured to extend from the body.

In some arrangements, the camera is rigidly mounted to the body.

In some arrangements, the camera is configured to pivot, rotate, or shift relative to the body.

In some arrangements, the camera includes an illumination source configured to emit light upon the subject to allow the camera to take one or more images of the subject.

In some arrangements, the camera is configured to take a first image of a side of the subject from a first position, and take a second image of the side of the subject from a second position different from the first position.

In some arrangements, a method for registering a transducer of a headset system with respect to a subject includes capturing image data of the subject, detecting one or more fiducial markers placed on the subject using the captured image data, and registering the transducer with respect to the subject based on the detected fiducial markers.

In some arrangements, a non-transitory computer-readable medium having computer-readable instructions, such that when executed, causes a processor of a headset system to register a transducer of the headset system by configuring a camera to capture image data of the subject, detecting one or more fiducial markers placed on the subject using the captured image data, and registering the transducer with respect to the subject based on the detected fiducial markers.

BRIEF DESCRIPTION OF THE FIGURES

Features, aspects, and advantages of the present disclosure will become apparent from the following description and the accompanying example arrangements shown in the drawings, which are briefly described below.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Figure 1A:
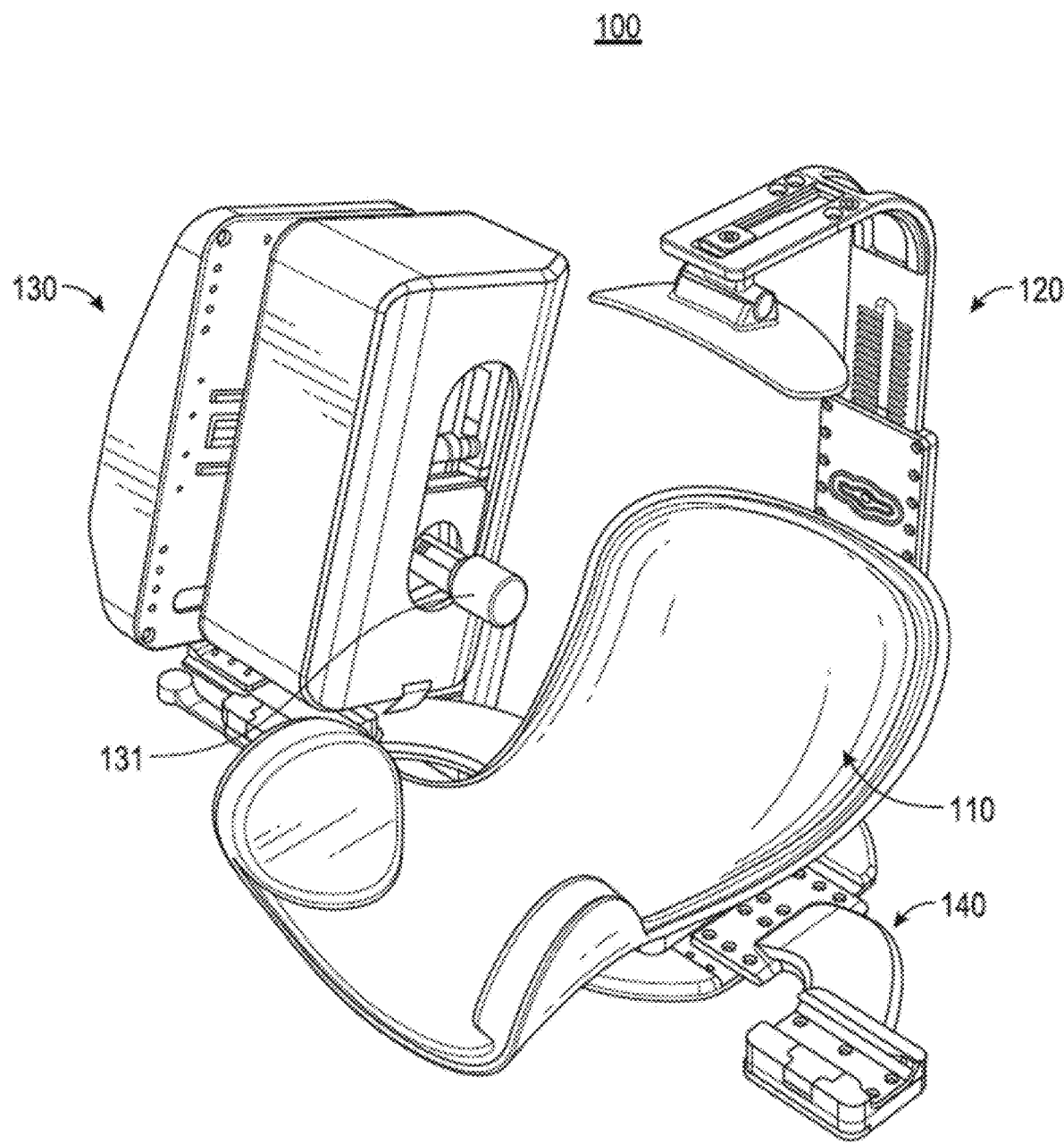
FIG. 1A illustrates a perspective view of a headset system including a device according to various arrangements.
Figure 1B:
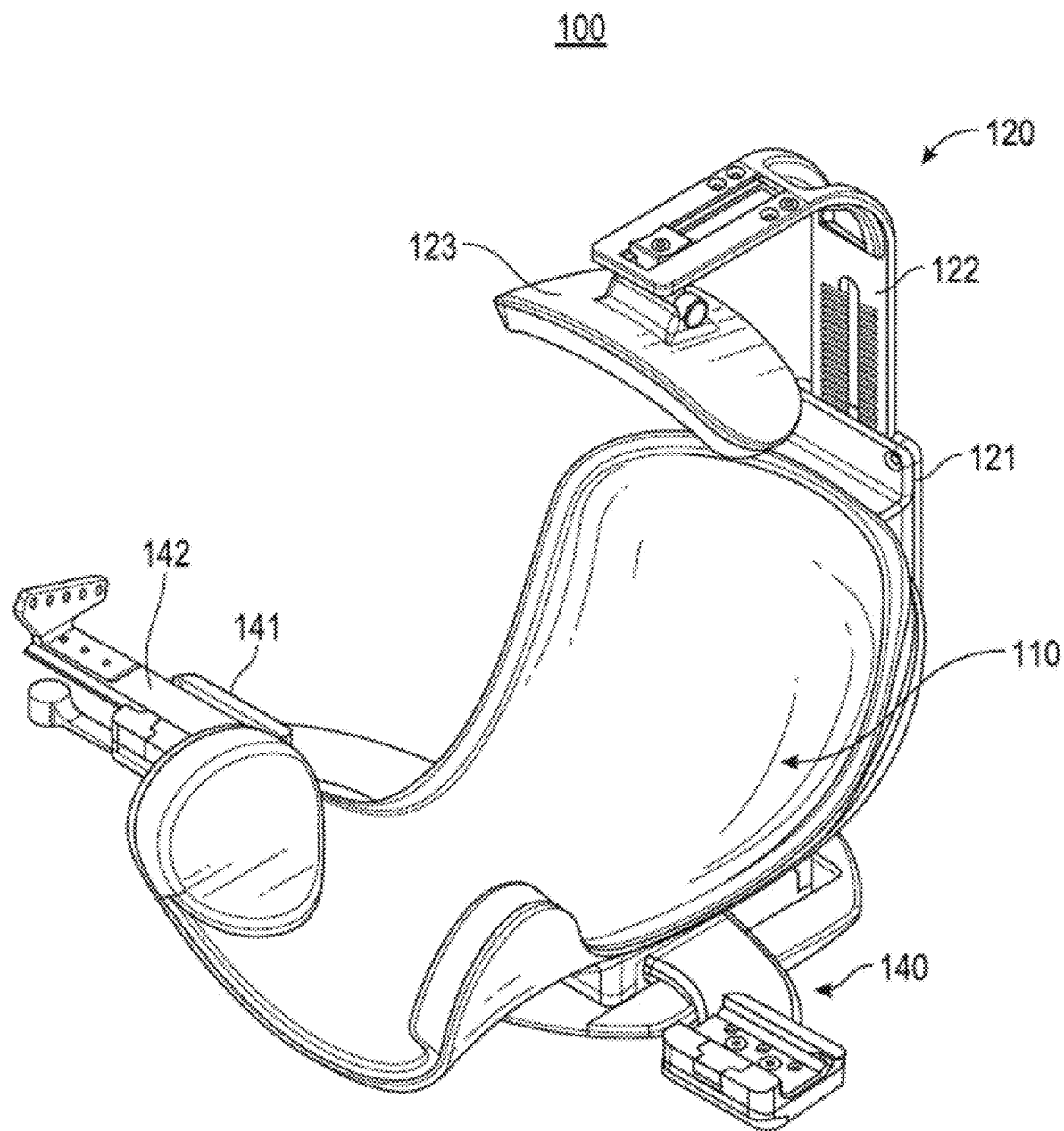
FIG. 1B illustrates a perspective view of the headset system illustrated in FIG. 1A without the device according to various arrangements.
Figure 2A:
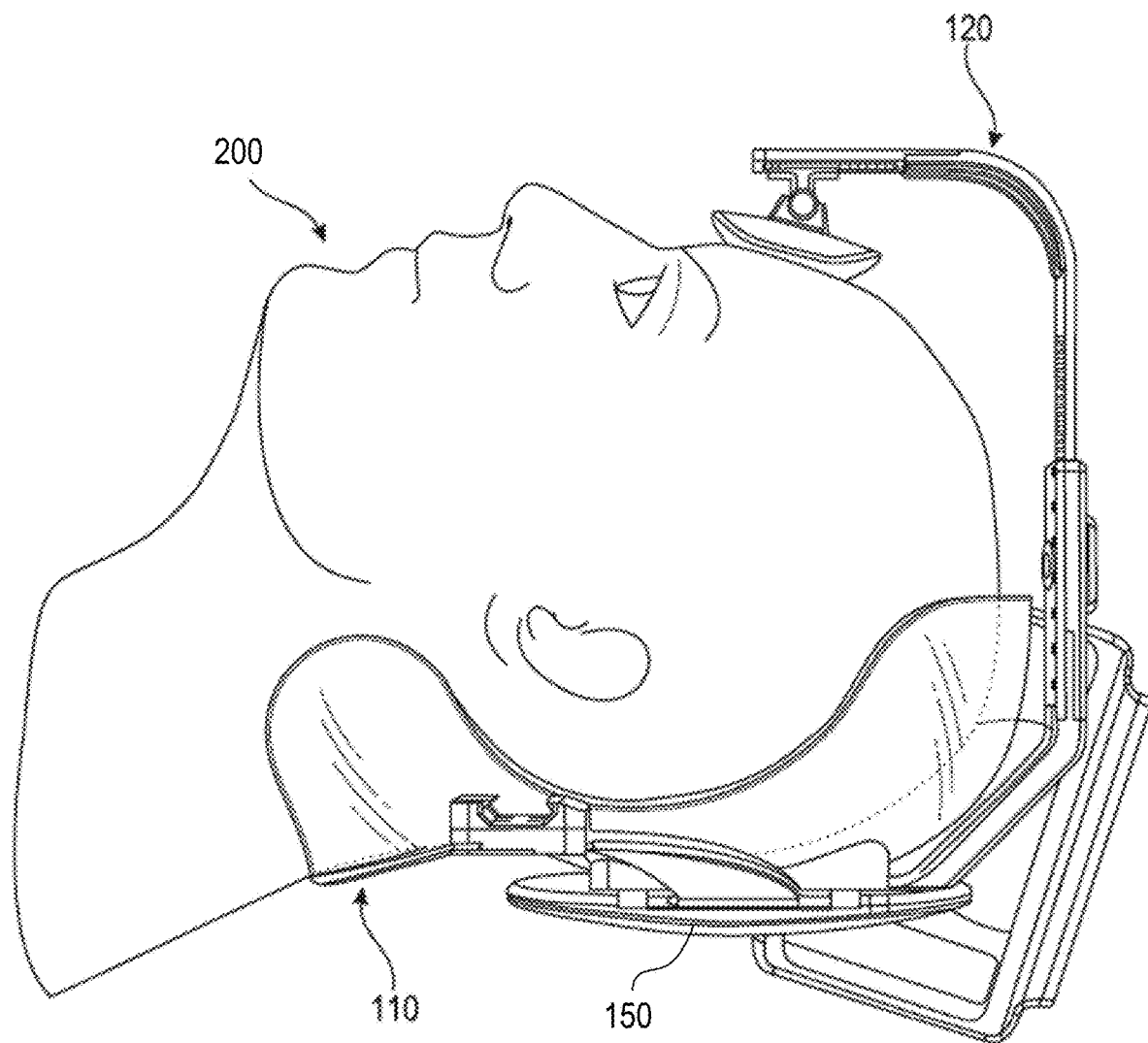
FIG. 2A, FIG. 2B, and FIG. 2C illustrate various views of the headset system illustrated in FIGS. 1A and 1B with a patient's head therein according to various arrangements.
Figure 2B:
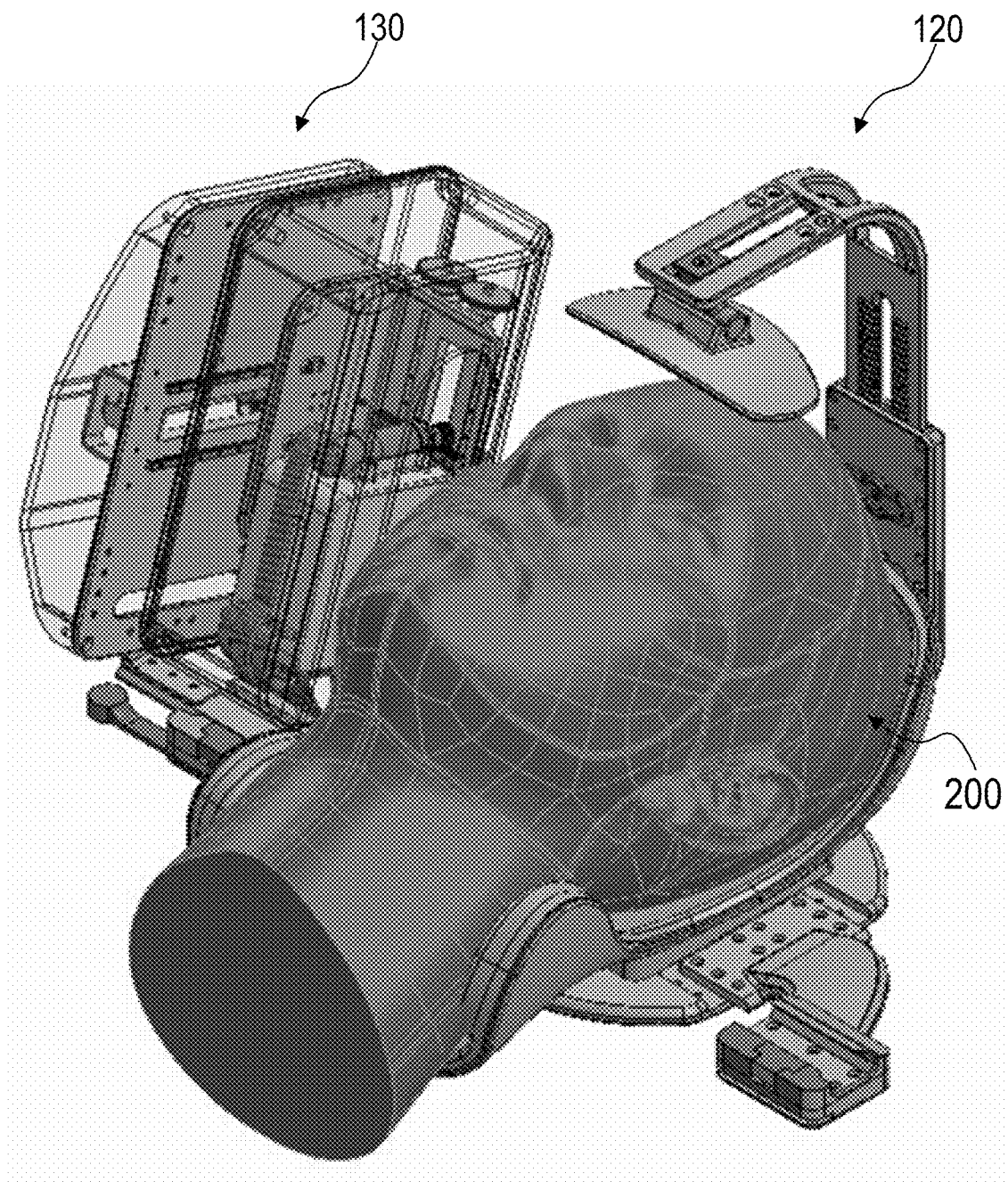
Figure 2C:
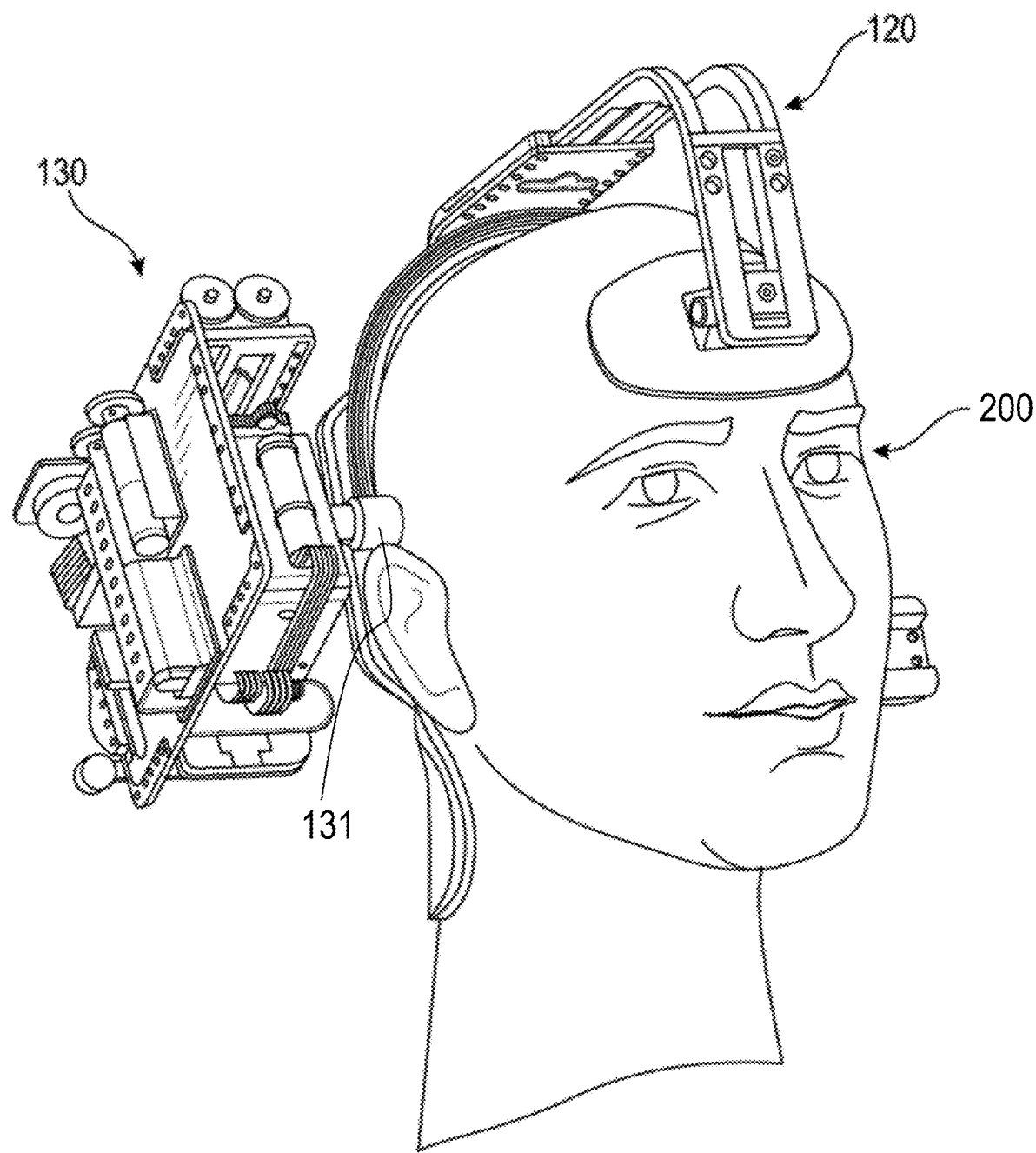

FIG. 1A illustrates a perspective view of a headset system 100 including a device 130 according to various arrangements. FIG. 1B illustrates a perspective view of the headset system 100 illustrated in FIG. 1A without the device 130 according to various arrangements. FIG. 2A, FIG. 2B, and FIG. 2C illustrate views of the headset system 100 illustrated in FIGS. 1A and 1B with a patient's head therein according to various arrangements.

Referring to FIGS. 1A-2C, in some arrangements, the dynamic headset system 100 includes a head cradle 110, a restraint system 120, the device 130, and a device attachment mechanism 140, and a mount 150. In some arrangements, the cradle 110 is configured to receive and support a patient's head (e.g., during operation of the device 130). The cradle 110 is capable of accommodating and supporting different head sizes for use in conjunction with the device 130. In some arrangements, the cradle 110 includes a frame and padding attached to the frame. The frame supports the padding, while the padding is configured to contact a human head. In some arrangements, the frame of the cradle 110 is shaped to suitably contour and support varying head sizes and shapes, and the frame is also shaped to adequately position a user's head in a workspace of the device 130. In some arrangements, the frame of the cradle 110 is made from any suitably malleable material that allows for flexing, such as, but not limited to, flexible plastics, polyethylene, urethanes, polypropylene, ABS, nylon, fiber-reinforced silicones, structural foams, or the like.

In some arrangements, the padding of the cradle 110 is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the padding of the cradle 110 has any suitable firmness for supporting a head, such as, but not limited to, in a range of about 0.1 pound per square inch (psi) to about 60 psi (e.g., in a range of about 0.1 psi to about 10 psi) or within other suitable ranges of firmness. In some arrangements, the padding of the cradle 110 has memory for expanding to fit contours of a head. In some arrangements, the padding (e.g., foam) of the cradle 110 is compressed and expands after a user's head is placed in the headset system 100 so that the padding expands to secure the headset apparatus 100. In some arrangements, the cradle 110 including the padding is manufactured by any suitable process for affixing the padding within the headset apparatus 110, such as, but not limited to, injection molding, laminating, adhesive mounting (e.g., gluing or bonding), co-molding, co-casting, injection, snapping, by Velcro fastening, by hook and loop fastening, friction fitting, attaching with barbs, using screw bosses, or the like.

In other arrangements, the padding of the cradle 110 includes an inflatable bladder. In some arrangements, the bladder is a hollow void that is filled manually or with a pump. In such arrangements, the inflatable bladder is self-inflating with an internal structure that has a memory and that expands within the bladder to inflate to at least 90% capacity. In other arrangements, the bladder is inflated to other suitable capacities, such as, but not limited to, at least about 95% capacity, at least about 80% capacity, at least about 70% capacity, and so on. In further arrangements, inflation is assisted with an integrated pump or an external filling or pumping source. In some arrangements, the inflatable bladder is filled with air, gas, liquid, or any other suitable element for affixing or securing the inflatable padding of the headset system 100 to a user's head. In other arrangements, the bladder is filled with plastic beads or pellets. In particular arrangements, the bladder that is filled with plastic beads or pellets becomes rigid, so as to capture a patient's head, when a vacuum is applied to the bladder.

In some arrangements, the restraint system 120 is configured to restrain a subject's head when placed in the cradle 110. In some arrangements, the restraint system 120 includes a base 121, a body 122, and a contact 123. In some arrangements, the base 121 is attached to the mount 150. The body 122 includes an elongated section that is configured to slide into the base 121, and lock while in the base 121, so as to provide adjustability of the restraint system 120 to accommodate different heads of subjects (e.g., different sizes and shapes). In some arrangements, the contact 123 is attached to the body 122, and the contact 123 is configured to contact and apply pressure against a subject's head (e.g., forehead) for securing the headset system 100 to the subject. In some arrangements, the contact 123 is configured to pivot at a location where the contact 123 is attached to the body 122 to provide further adjustability for different sized and shaped heads of subjects. The contact 123 includes a padding for contacting a subject's head, and the padding is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like.

In some arrangements, the device 130 is modular and can be attached and detached from the headset system 100 via the attachment mechanism 140. In some arrangements, the headset system 100 is used in conjunction with a medical device for use with respect to a user's head (e.g., an ocular monitoring system, a breathing device, a device for monitoring neurological activity, a surgical device, a device for monitoring radioactive traces, or any other appropriate device). In other arrangements, the headset system 100 is used in conjunction with a non-medical device for use with respect to a user's head (e.g., a virtual reality eyepiece).

In some arrangements, the device 130 includes a transducer or a probe 131 and robotics for controlling the probe 131, collectively referred to as an "instrument." In that regard, "instrument" as used herein refers to at least one data collection device (e.g., a probe such as but not limited to, the probe 131) and devices (e.g., positioning components such as but not limited to, the robotics 132) configured to control position and operations (e.g., data collection) of the data collection device. For example, the robotics are configured to translate the probe 131 along a surface of a head and to move the probe 131 towards and away from the head. In some arrangements, an end of the probe 131 interfaces with the robotics, and the robotics include components, such as, but not limited to, a motor assembly and the like for controlling the probe 131 (e.g., control z-axis pressure, normal alignment, or the like of the probe 131). In some arrangements, the registration of the probe 131 against a subject's head is accomplished using the robotics to properly position and align the probe 131 with the subject's head.

In some arrangements, the probe 131 includes a first end and a second end that is opposite to the first end. In some arrangements, the first end includes a concave surface that is configured to be adjacent to or contact a scanning surface (e.g., a head of a subject). The concave surface is configured with a particular pitch to focus generated energy towards the scanning surface. In some arrangements, the device 130 is a Transcranial Doppler (TCD) apparatus such that the first end of the probe 131 is configured to be adjacent to or contact and align along a human head (e.g., a side of the human head), and the first end of the probe 131 is configured to provide ultrasound wave emissions from the first end and directed into the human head (e.g., towards the brain). In that regard, the probe 131 is an ultrasound probe configured for ultrasound procedures. In other arrangements, the probe 131 is configured to emit other types of waves during operation, such as, but not limited to, infrared, x-rays, electromagnetic, thermal, near-infrared, optical, lighting, audio, electroencephalography, or the like.

In some arrangements, the second end of the probe 131 is coupled to the robotics. In some arrangements, the second end of the probe 131 includes a threaded section along a portion of the body of the probe 131, and the second end is configured to be secured in the robotics via the threads (e.g., by being screwed into the robotics). In other arrangements, the probe 131 is secured in the robotics by any other suitable connecting means, such as, but not limited to, welding, adhesive, one or more hooks and latches, one or more separate screws, press fittings, or the like.

Further disclosure regarding probe systems that can be used in conjunction with the headsets described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety.

In some arrangements, the headset system 100 holds other medical and non-medical devices that are used and registered (e.g., positioned or aligned) with respect to a user's head. For example, in some arrangements, an ocular device is a device that is optimized by being properly positioned and aligned with a user's eyes (e.g., if the ocular device is shifted with respect to a user's eyes, performance of the ocular device may decline). In some arrangements, the ocular device is attached at the headset system 100 so as to cover the eyes of a patient. As an example of a non-medical device use with respect to the headset system 100, in some arrangements, the headset system 100 can be used in connection with the ocular device that is a virtual reality device configured to provide a virtual experience to the user such that any disturbance of the positioning of the ocular device in front of the user's eyes may cause a degradation in the user's virtual experience.

In some arrangements, the ocular device is a medical device designed to track ocular behavior of a subject (e.g., to diagnose whether the user has experienced a concussion). In other arrangements, the ocular device is an ocular diagnosis or treatment tool for determining or adjusting vision of the user. As an example, the ocular device is a device for correcting imperfect vision of a user (e.g., laser eye surgery). As another example, in some arrangements, the ocular device is an ocular diagnostic tool for determining a vision prescription of a user, presence of one or more eye conditions (e.g., glaucoma, cataracts, ocular hypertension, uveitis, or the like), and the like. In some arrangements, the ocular device is designed to cover and interact with both eyes simultaneously or in sequence. In other arrangements, the ocular device is designed to cover and interact with a single eye (e.g., while the other eye remains uncovered).

In some arrangements, the attachment mechanism 140 is configured to receive and secure the device 130. In other arrangements, the attachment mechanism 140 is configured to receive and secure other medical and non-medical devices (e.g., those discussed above). In some arrangements, the attachment mechanism 140 includes a track 141 and a slider 142. The track 141 receives the slider 142 and the slider 142 is adjustable along the track 141. For example, the slider 142 can slide within the track 141 and can be locked in place at a desired location. In some arrangements, the attachment mechanism 140 includes two sets of the track 141 and the slider 142, with each set located at an opposite side of the headset system 100. Accordingly, in some arrangements, a plurality of devices 130 can be attached at the headset system 100 for operation with respect to both sides of a subject's head.

In some arrangements, the device 130 is affixed to the slider 142 so that adjustment of the slider 142 results in adjustment of the device 130 with respect to a subject's head (e.g., telescoping adjustment towards and away from the subject's head). In some arrangements, the bottom of the device 130 is connected to the slider 142. In particular arrangements, the device 130 is affixed to the attachment mechanism 140 by any suitable connection mechanism, such as, but not limited to, welding, adhesive, one or more separate bolts, one or more hooks and latches, one or more separate screws, press fittings, or the like. In some arrangements, the attachment mechanism 140 (e.g., the track 141 and/or the slider 142) is made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like.

In some arrangements, the mount 150 is affixed to the restraint system 120 (e.g., the base 121), the attachment mechanism 140, and the cradle 110. In some arrangements, one or more of the restraint system 120, the attachment mechanism 140, and the cradle 110 are attached to the mount 150 via a plurality of screws and/or bolts. In other arrangements, one or more of the restraint system 120, the attachment mechanism 140, and the cradle 110 are attached to the mount 150 by any other suitable connecting means, such as, but not limited to, welding, adhesive, one or more hooks and latches, press fittings, or the like. In some arrangements, one or more of the restraint system 120, the attachment mechanism 140, and the cradle 110 are permanently affixed to the mount 150. In other arrangements, one or more of the restraint system 120, the attachment mechanism 140, and the cradle 110 are releasably attached to the mount 150.

In some arrangements, the mount 150 is made from any suitable rigid material, such as, but not limited to, hard plastic, metals, aluminum, steel, titanium, magnesium, various alloys, rigid plastics, composites, carbon fiber, fiber glass, expanded foam, compression molded foam, SLA or FDM-made materials, RIM molding, ABS, TPO, nylon, PVC, fiber reinforced resins, or the like. Further disclosure regarding the cradle, the mount, and other structural components of the system 100 can be found in non-provisional patent application Ser. No. 15/853,433, titled HEADSET SYSTEM, and filed on Dec. 22, 2017, and non-provisional patent application Ser. No. 16/101,352, titled DYNAMIC HEADSET APPARATUS, and filed on Aug. 10, 2018 each of which is incorporated herein by reference in its entirety.

Figure 3A:
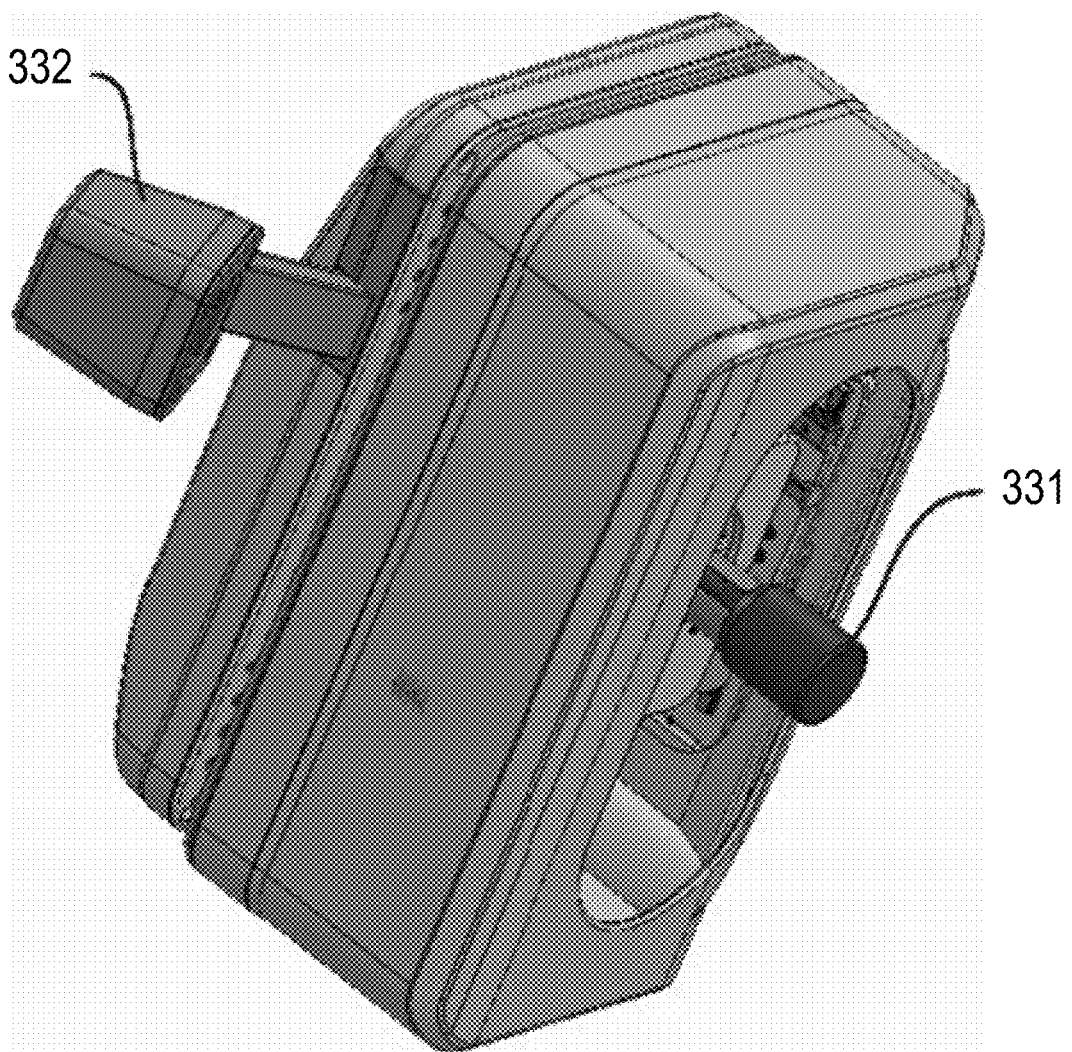
FIG. 3A illustrates a perspective view of a device included in a headset system according to various arrangements.
Figure 3B:
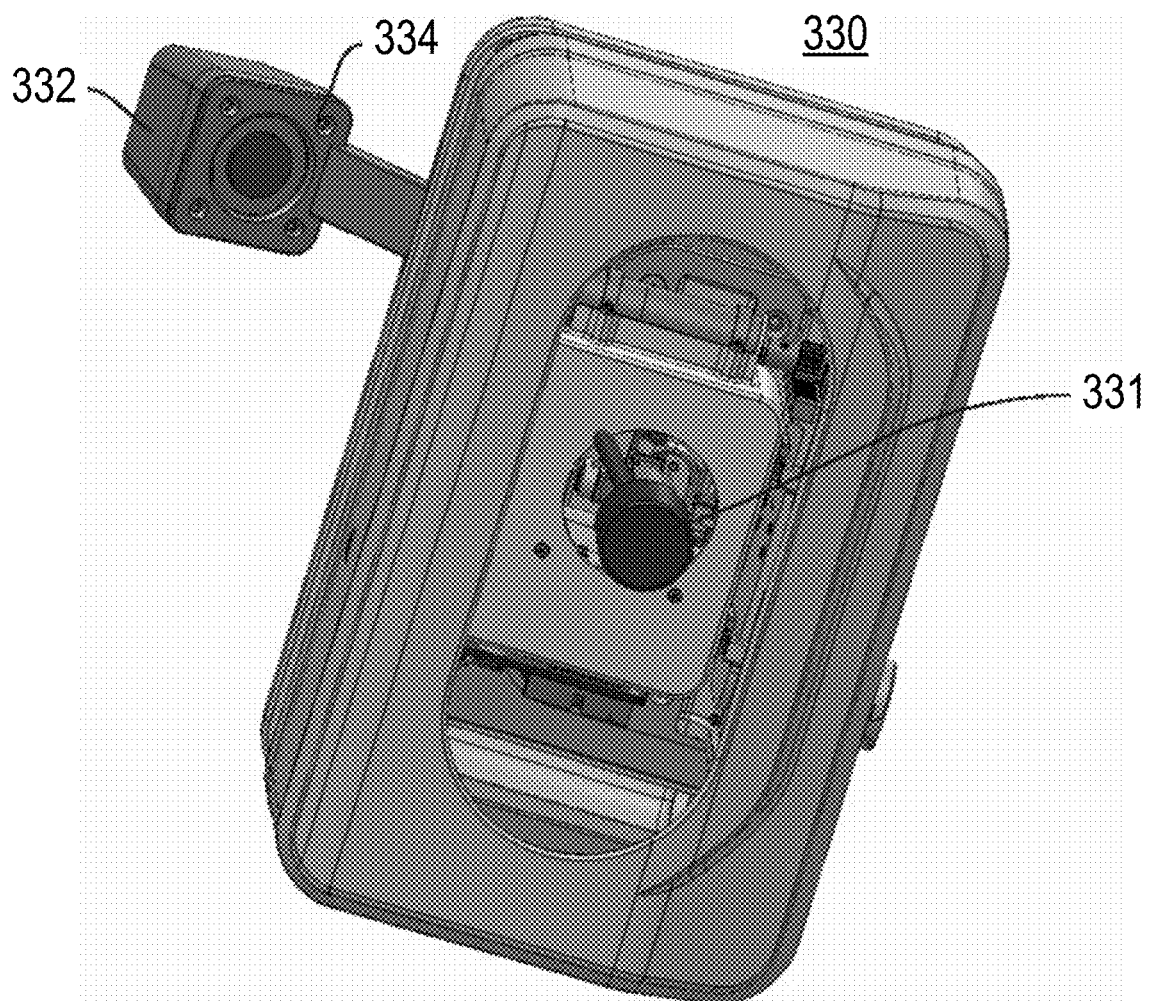
FIG. 3B illustrates a front view of the device illustrated in FIG. 3A according to various arrangements.
Figure 3C:
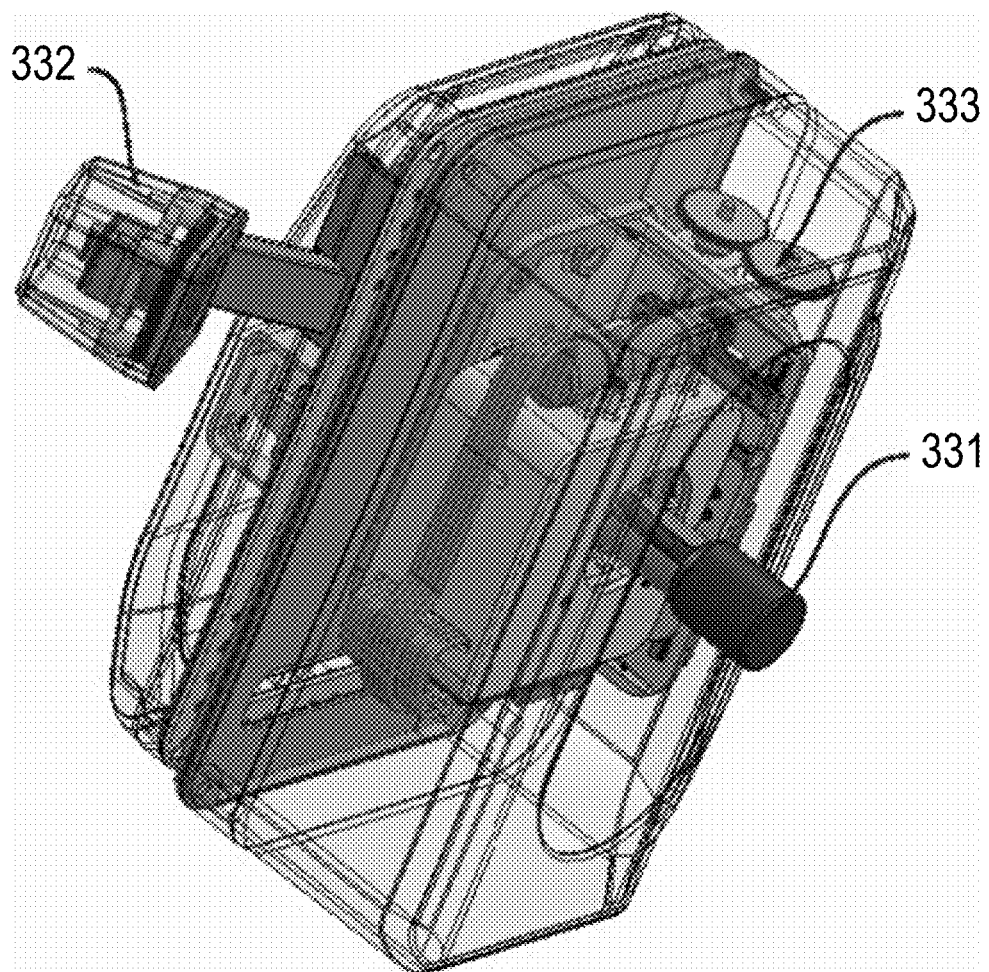
FIG. 3C illustrates a transparent perspective view of the device illustrated in FIG. 3A according to various arrangements.
Figure 3D:
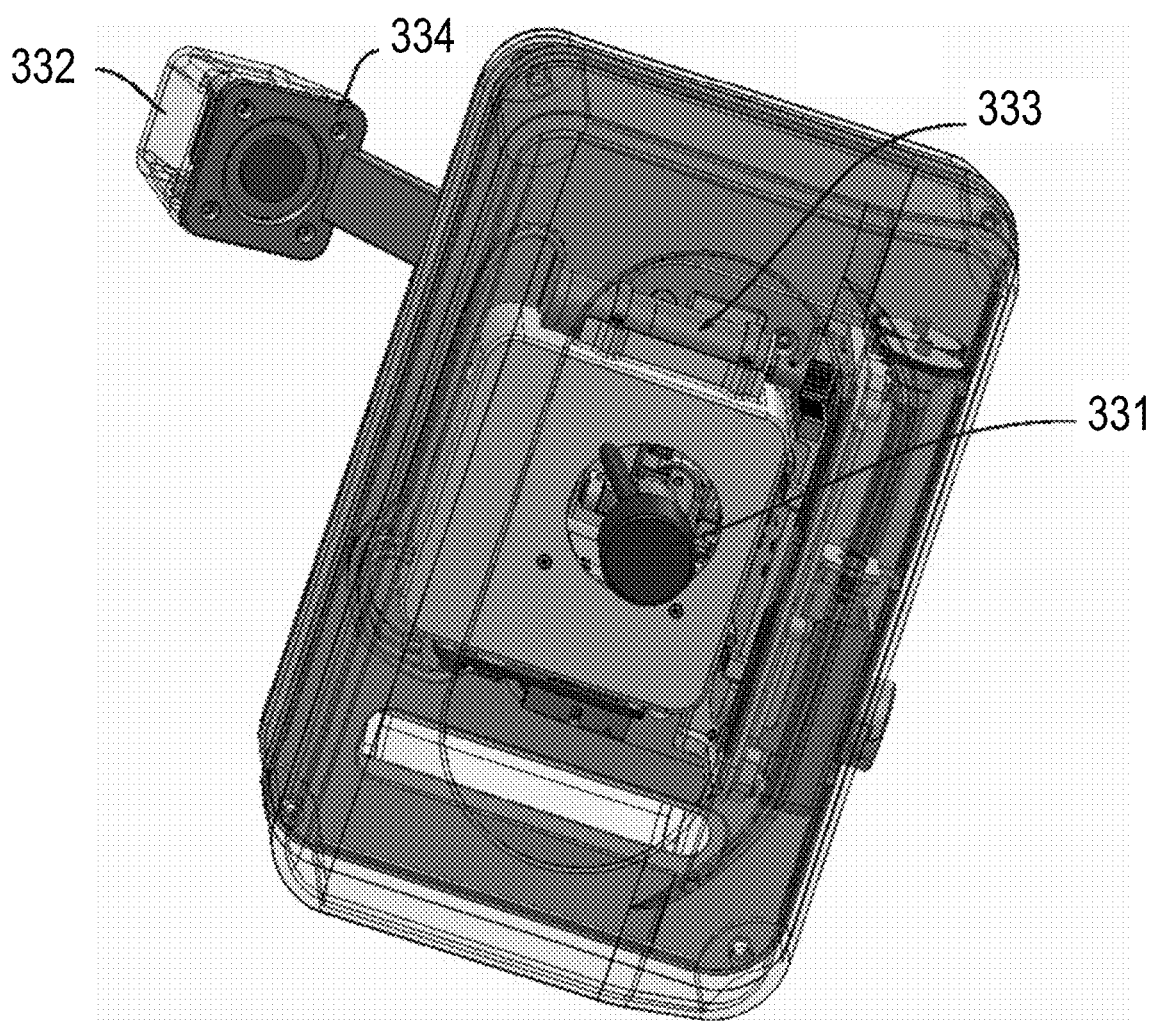
FIG. 3D illustrates a transparent front view of the device illustrated in FIG. 3A according to various arrangements.

FIG. 3A illustrates a perspective view of a device 330 included in a headset system according to various arrangements. FIG. 3B illustrates a front view of the device 330 illustrated in FIG. 3A according to various arrangements. FIG. 3C illustrates a transparent perspective view of the device 330 illustrated in FIG. 3A according to various arrangements. FIG. 3D illustrates a transparent front view of the device 330 illustrated in FIG. 3A according to various arrangements. Referring to FIGS. 1-3D, the device 330 is an example implementation of the device 130.

In some arrangements, the device 330 is configured to be coupled to the attachment mechanism 140 as described above, for use within the headset system 100 (e.g., similar to the device 130). In some arrangements, the device 330 includes a transducer or probe 331, a camera 332, and robotics 333. In some arrangements, the probe 331 is similar to the probe 131, and so the description above with respect to the probe 131 is applicable to the probe 331. As shown, in some arrangements, the probe 331 is coupled to the robotics 333 of the device 330 such that the probe 331 is moved along multiple axes (e.g., x-axis, y-axis, and z-axis), as described above.

In some arrangements, the camera 332 is configured to capture one or more images of a subject's head when the subject's head is placed within the headset system 100 (e.g., within the cradle 110). From the captured one or more images, the subject's head can be registered with respect to the device 330 (e.g., the device 330 can initially position or align the probe 331 for subsequent operation of the probe 331 and the device 330 on the subject's head, restricting or defining the workspace of the probe 331 to certain boundaries during operation of probe 331 and the device 330, and so on). Further details regarding registration of the device 330 is disclosed below.

In some arrangements, the camera 332 is any suitable image capturing mechanism or device for taking images of one or more body parts of the subject (e.g., a subject's head). Examples of the camera 332 include but are not limited to, a digital camera, a thermal camera, an infrared camera, a night vision camera, and the like. In some examples, the camera 332 can have any suitable resolution and focal length for capturing desired images configured to our can be suitable for registering a subject's head (e.g., about 5 megapixels and about 4 millimeter (mm) focal length). In particular arrangements, the resolution and/or the focal length of the camera 332 is fixed or predetermined. In other arrangements, the resolution and/or the focal length are variable. In some arrangements, the camera 332 moves (e.g., extends) from a main body of the device 330 (e.g., a portion of the device 330 housing the robotics 333 and the probe 331) and is rigidly mounted to the device 330 (e.g., to a portion of the main body of the device 330 configured to extend from the main body). In other arrangements, the camera 332 is adjustable with respect to the main body of the device 330 (e.g., the camera 332 can pivot, rotate, shift, and the like relative to the main body).

In some arrangements, the camera 332 is positioned or moved (e.g., extended, pivoted, rotated, or shifted) automatically by a controller (a controller 408 of FIG. 4) or by an operator manually such that particular anatomical locations of a subject's head are within a field of view of the camera 332 when the subject's head is held within the headset system 100, and such that the device 330 or any other portion of the headset system 100 does not obstruct the field of view of the camera 332. For example, in some arrangements, the subject's tragus and eye are configured to be visible to the camera 332 when the subject's head is held within the headset system 100. In some arrangements, the relative location and rotation of the camera 332 relative to the workspace of the probe 331 and the robotics 333 is a known and fixed parameter that can be utilized to register the device 330 with respect to a subject's head, as further discussed below. In further arrangements, an exposure time of the camera 332 is adjustable (e.g., manually adjustable by an operator).

In some arrangements, the camera 332 includes an illumination source 334 configured to emit light to be irradiated upon the subject's head to allow the camera 332 to take one or more images of the subject's head. In some arrangements, the illumination source 334 includes one or more illuminators (e.g., one or more light-emitting diodes (LEDs), one or more fluorescent lights, one or more Ballast lights, one or more halogen lights, one or more neon lights, and the like). The illumination source 334 includes any desired number of illuminators for suitably illuminating a subject's head such that the camera 332 can obtain images of a subject's head, as described herein. For example, the illumination source 334 can include a plurality of illuminators (e.g., two, four, eight, twelve, or more illuminators). In some arrangements, the light emitted from the illumination source 334 has a suitable wavelength for being captured by the camera 332, such as, but not limited to, that of infrared light (e.g., light having a wavelength of 850 nanometers (nm)). Accordingly, in some arrangements, the camera 332 is sensitive to light having a wavelength of that of light emitted by the illumination source 334 (e.g., the camera 333 is sensitive to infrared light). In some arrangements, the illuminators of the illumination source 334 are safe enough to irradiate light upon eyes of subjects and operators for a suitable amount of time at a suitable distance (e.g., for 1000 seconds at a distance of 50 mm or greater). In other arrangements, no illumination source is needed and the camera 332 (e.g., a night vision camera, an infrared camera, a thermal camera, and so on) is configured to capture images of the subject's head without illumination.

In some arrangements, the illumination source 334 includes a printed circuit board (PCB) on which the illuminators are located. In particular arrangements, the PCB includes an opening for allowing the lens of the camera 334 to pass therethrough. In some arrangements, the illuminators are arranged to be evenly spaced (e.g., in a circular formation) around the lens of the camera 334, and the illuminators are further positioned to be as close as possible to the outer diameter of the lens of the camera 334. In some arrangements, the brightness of the illumination source 334 is adjusted using Pulse Width Modulation (PWM) and can be adjusted by an operator or can be automatically adjusted (e.g., based on brightness of ambient light). In some arrangements, the illuminators are powered in an on state when a frame exposure of the camera 334 is active.

Figure 4:
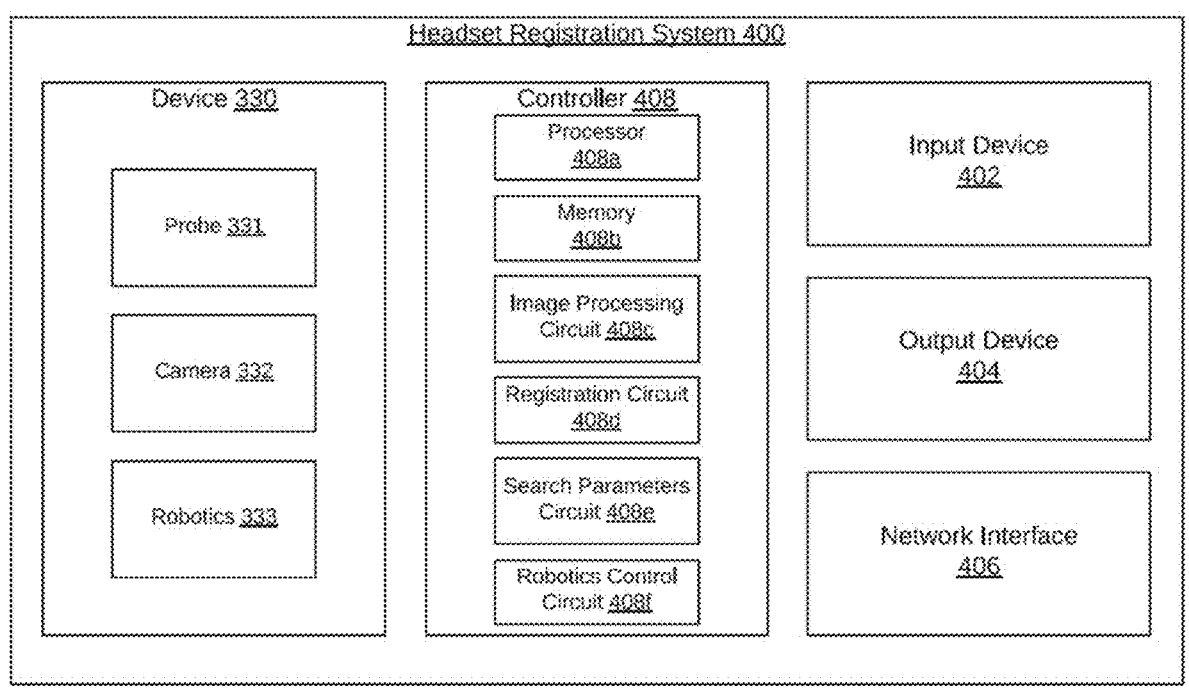
FIG. 4 illustrates a block diagram of a headset registration system according to various arrangements.

FIG. 4 illustrates a block diagram of a headset registration system 400 according to various arrangements. Referring to FIGS. 1A-4, in some arrangements, the headset registration system 400 is an example implementation of the headset system 100 and includes the device 330 including the probe 331, the camera 332, and the robotics 333, which are described herein. The headset registration system 400 further includes an input device 402, an output device 404, and a network interface 406.

In some arrangements, the input device 402 includes any suitable device configured to allow an operator to input information or commands into the headset registration system 400. In some arrangements, the input device 402 includes, but is not limited to, a keyboard, a keypad, a mouse, a joystick, a touchscreen display, or any other input device performing a similar function. In some arrangements, the output device 404 includes any suitable device configured to display information, results, messages, and the like to an operator concerning the headset registration system 400. In some arrangements, the output device 404 includes, but is not limited to, a computer monitor, a printer, a facsimile machine, or any other output device performing a similar function. In some arrangements, the input device 402 and the output device 404 are the same device (e.g., a touchscreen display device). In some arrangements, the network interface 406 is structured for sending and receiving data over a communication network (e.g., results, instructions, requests, software or firmware updates, and the like). Accordingly, the network interface 406 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

In some arrangements, the headset registration system 400 includes a controller 408 for controlling operations, processing data, executing input commands, providing results, and the like with respect to the headset registration system 400. For example, the controller 408 is configured to receive input data or instructions from the input device 402 or the network interface 406, control the device 330 to execute the commands, receive data from the device 330, provide information to the output device 404 or network interface 406, and so on. In some arrangements, the controller 408 includes a processor 408a, memory 408b, an image processing circuit 408c, a registration circuit 408d, a search parameters circuit 408e, and a robotics control circuit 408f. In particular arrangements, the headset system 100 includes a plurality of cameras 332 (e.g., at each side of the headset system 100) such that the headset system 100 is bilateral and such that images of both sides of a subject's head are captured. In such arrangements, the captured images are processed at the single controller 408 (e.g., each of the left and right images of the subject's head is processed independently at the controller 408).

In some arrangements, the processor 408a is implemented as a general-purpose processor and is coupled to at least one memory 408b. The processor 408a includes any suitable data processing device, such as a microprocessor. In the alternative, the processor 408a includes any suitable electronic processor, controller, microcontroller, or state machine. In some arrangements, the processor 408a is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 408a is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 408b includes a non-transitory processor-readable storage medium that stores processor-executable instructions. In some arrangements, the memory 408b includes any suitable internal or external device for storing software and data. Examples of the memory 408b can include, but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 408b can store an Operating System (OS), user application software, and/or executable instructions. The memory 408b can also store application data, such as an array data structure. In some arrangements, the memory 408b stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

Figure 5A:
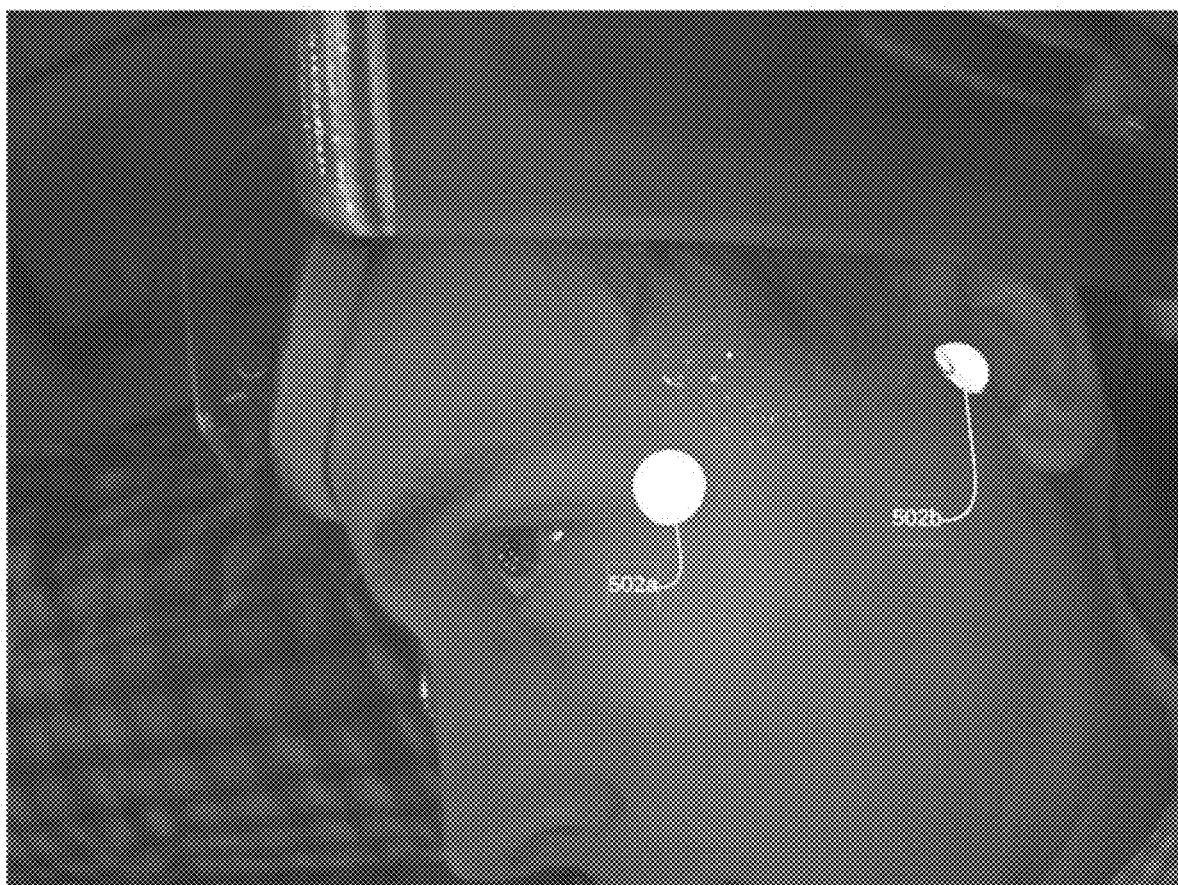
FIG. 5A illustrates an image taken by a camera of a device according to various arrangements.

FIG. 5A illustrates an image 500a, which is an example of an image that can be taken by the camera 332 of the device 330 according to various arrangements.

Referring to FIGS. 1A-5A, in some arrangements, the image processing circuit 408c is configured to receive image data taken by the camera 332 (e.g., an image depicting a side of a subject's head). For example, the image captured by the camera 332 includes a two-dimensional array of pixel brightness values. In some arrangements, the subject's head has fiducial markers (or fiducials) disposed by an operator at anatomically significant locations such that the image includes the subject's head with the fiducials. In some arrangements, the fiducials are disposed at anatomically significant locations so as to signify the boundaries of the workspace of the device 330 during operation, and the fiducials are configured to be detected by the image processing circuit 408c. In particular arrangements, the fiducials are disposed at a corner of a subject's eye and at the tragus of the subject. As such, to estimate image locations of anatomical markers (e.g., ears and eyes) relative to the probe 331 through detection of fiducials, at least one image per lateral side of the subject's head can be obtained after placement of at least one fiducial on either lateral side of the subject's head. In other arrangements, fiducial markers can be any nature anatomy landmarks such as but not limited to, the eyes, the nose, the ear, the forehead, the eyebrow, the mouth, the lips, the hairline, the collar bone, the navel, the nipples, any joints, fingernails, and the like.

The image 500 depicts a first fiducial 502a and a second fiducial 502b. In some arrangements, any suitable number of fiducials can be disposed on a subject, such as, but not limited to, one fiducial or three or more fiducials. In some arrangements, the fiducials 502a, 502b are adhesive stickers having a fixed, known, or predetermined size, shape, color, and design to allow the controller 408 to identify the fiducials 502a and 502b. In some arrangements, all fiducials disposed on the body of the subject have the same size, shape, color, and design. The controller 408 is preprogrammed with the fiducials characteristics such as the size, shape, color, and design to identify the fiducials from the captured images. In some arrangements, the fiducials 502a, 502b include a circular retroreflective material and a surrounding black ring. The circular retroreflective material and the surrounding black ring of each of the fiducials 502a, 502b are on a surface opposite of the surface on which adhesive is provided, such that the circular retroreflective material and the surrounding black ring are configured to the camera 332 when the fiducials 502a, 502b are placed on the head of the subject. For example, the retroreflective fiducials 502a, 502b are capable of reflecting light back to a source of the light (e.g., the illumination source 334) with minimal scattering. As a particular example, an electromagnetic wavefront incident on the fiducials 502a, 502b is reflected back along a vector that is parallel to but opposite in direction from the wave's source. In some arrangements, the fiducials 502a, 502b are consumable or disposable items.

While the fiducials 502a, 502b are described to have a circular shape, other shapes such as but not limited to, a square, a rectangle, a triangle, a cross, a star, or another complex design that can be easily distinguished from other shapes present on the body of the subject by the controller 408. An example of a complex design is a square within a circle, which is within a triangle.

In some arrangements, the size of the fiducials 502a, 502b is a known and controlled parameter that is utilized by the controller 408 during image processing and registration. In some arrangements, each of the fiducials 502a, 502b has a distinctive boundary (e.g., a black boundary) that is made from a material that is not heavily reflective or minimally reflective such that there can be a high contrast between the retroreflective material and its minimally-reflective boundary during illumination of the subject's head (e.g., by the illumination source 334). The boundary is around an outer perimeter of each of the fiducials 502a and 502b. In some arrangements, each of the fiducials 502a, 502b includes an adhesive backing for application to a subject's skin such that the fiducials 502a, 502b sufficiently remain in place during operation of the device 330. Similarly, the color, the shape, and design of the fiducials 502a, 502b is a known and controlled parameter that is utilized by the controller 408 during image processing and registration.

In some arrangements, the image processing circuit 408c is configured to process the images taken by the camera 332 (e.g., by detecting the fiducials 502a, 502b captured in the image 500a). In some arrangements, the image 500a is preprocessed to smooth the image 500a. For example, a blue filter can be applied to the image 500a to smooth out the effects of noise that is typically present in a digital image.

In some arrangements, the image processing circuit 408c is configured to create one or more binary images from the preprocessed image (e.g., the digital image). In particular arrangements, a threshold-based binary image is created, for example, in which a value of each pixel of the image 500a whose brightness is above a predetermined brightness threshold is set to 255 and a value of each pixel whose brightness is below the predetermined brightness threshold is set to 0. In further arrangements, an edge detection-based binary image is created, for example, by using a Canny edge detection process, in which a pixel of the image 500a is set to a 1 if it lies upon a part of the image 500a recognized as being an edge in the preprocessed image and a 0 if the pixel is detected as not lying upon an edge. In other arrangements, any suitable edge detection process can be used to create the edge detection-based binary image. In some arrangements, the threshold-based binary image is created, while the edge detection-based binary image is not created. In other arrangements, the edge detection-based binary image is created, while the threshold-based binary image is not created. In other arrangements, both the threshold-based binary image and the edge detection-based binary image are created.

In some arrangements, the one or more generated binary images are post-processed. For example, in particular arrangements, a dilation filter and/or an erosion filter are applied to the binary images such that white regions are grown and/or shrunk, respectively, as desired.

In some arrangements, contours within the one or more generated binary images are detected, and of the detected contours, those (fiducial contours) that are proper fiducials are selected. Unselected contours may belong to artifacts created by backgrounds of the images or light reflections on the subject's face. For example, in particular arrangements, each contour is replaced with its convex hull such that the contour is a closed shape with a well-defined area, and a best fit ellipse is computed for each contour. In some arrangements, different detected contours that have best fit ellipses that are the same size and that have the same center point (e.g., within specified tolerances) are consolidated and treated as being the same contour. In some arrangements, contours each having a ratio of their area to their perimeter (e.g., an area-to-perimeter ratio) that differs by a particular amount from a ratio of the area to perimeter (e.g., an area-to-perimeter ratio) for a perfect circle are rejected (e.g., if the area to perimeter ratio of a contour differs by more than a predetermined threshold amount from the area to perimeter ratio for a perfect circle, the contour is rejected). For example, this is because each of the fiducials 502a, 502b is known to be implemented as a perfect circle in some arrangements. Similarly, fiducials of other shapes such as but not limited to, a square, a rectangle, a triangle, a cross, a star, or another complex design can be identified based on an acceptable deviation threshold with respect to each respective shape similar to described herein with respect to a perfect circle. In some arrangements, ellipses having an area outside a predetermined range of values are rejected (e.g., a range of values corresponding to the known areas of the fiducials 502a, 502b). In some arrangements, contours that have an area that differs by greater than a threshold ratio from an area of the best fit ellipse are rejected. In some arrangements, any one or more (or all) of the above-described contour and ellipse rejection processes are utilized.

In some arrangements, contours such as the ellipses (e.g., the fiducials) that are detected as being present in both the threshold-based binary image and the edge detection-based binary image are accepted. For example, in particular arrangements, ellipses are identified as being present in both images if ellipse center points that are detected in each binary image are determined to be within a predetermined range of one another. Accordingly, in some arrangements, the results of the image processing operation include a collection of feature tuples capturing location and size of pixels of each fiducial in an image.

In some arrangements, the fiducial size to proceed with is selected based on the sizes detected in each binary image, for example, in a case where the threshold-based binary image and the edge detection-based binary image are in conflict regarding fiducial size. In particular arrangements, the fiducials (e.g., sizes of fiducials) of the threshold-based binary image are always selected. In other arrangements, the fiducials of the edge detection-based binary image are always selected. In yet other arrangements, the smaller-sized fiducials are always selected, the larger-sized fiducials are always selected, a mean of the differing-sized fiducials are selected, and so on.

Figure 5B:
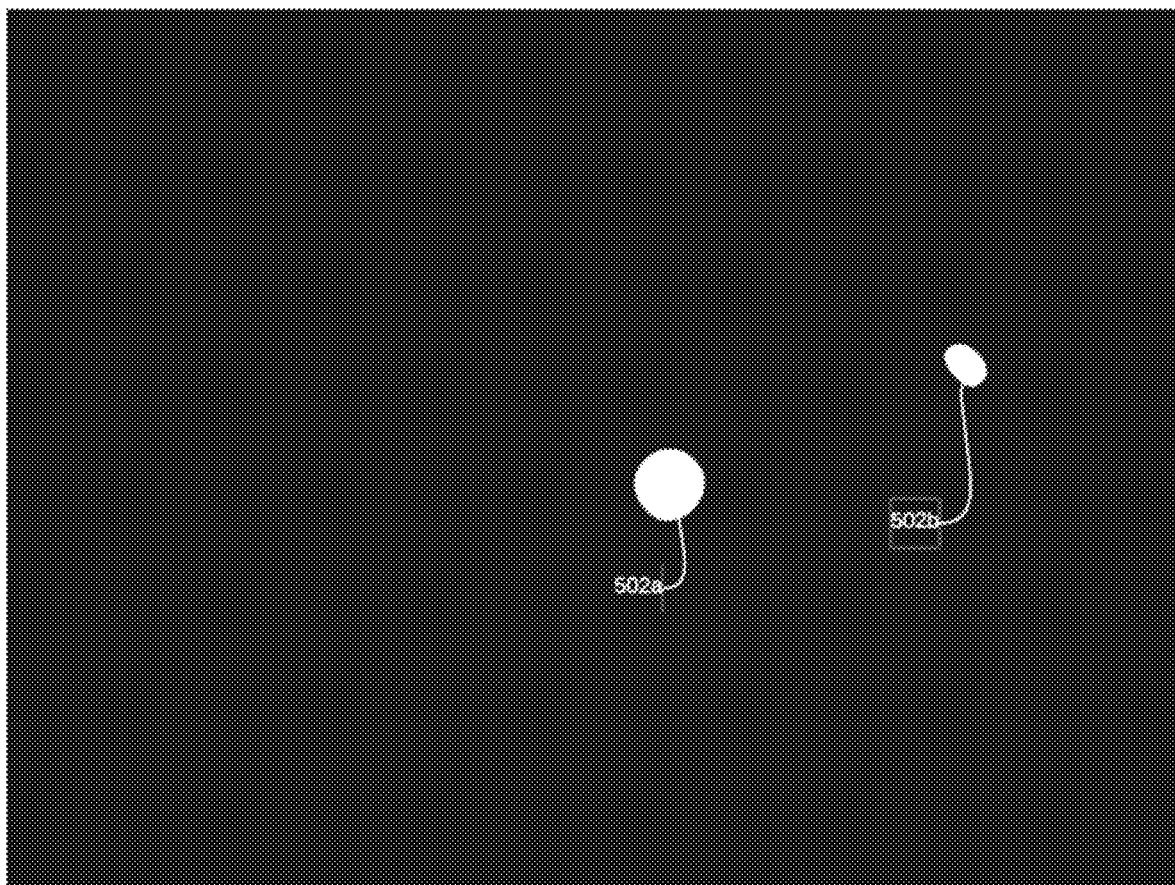
FIG. 5B illustrates a binary image after the image shown in FIG. 5A undergoes image processing according to various arrangements.

FIG. 5B illustrates a binary image 500b after the image 500a shown in FIG. 5A undergoes image processing according to various arrangements. Referring to FIGS. 1A-5B, in some arrangements, by utilizing the above-described image processing techniques, the image processing circuit 408c is configured to generate the binary image 500b that distinctly identifies and locates the fiducials 502a, 502b.

Figure 6:
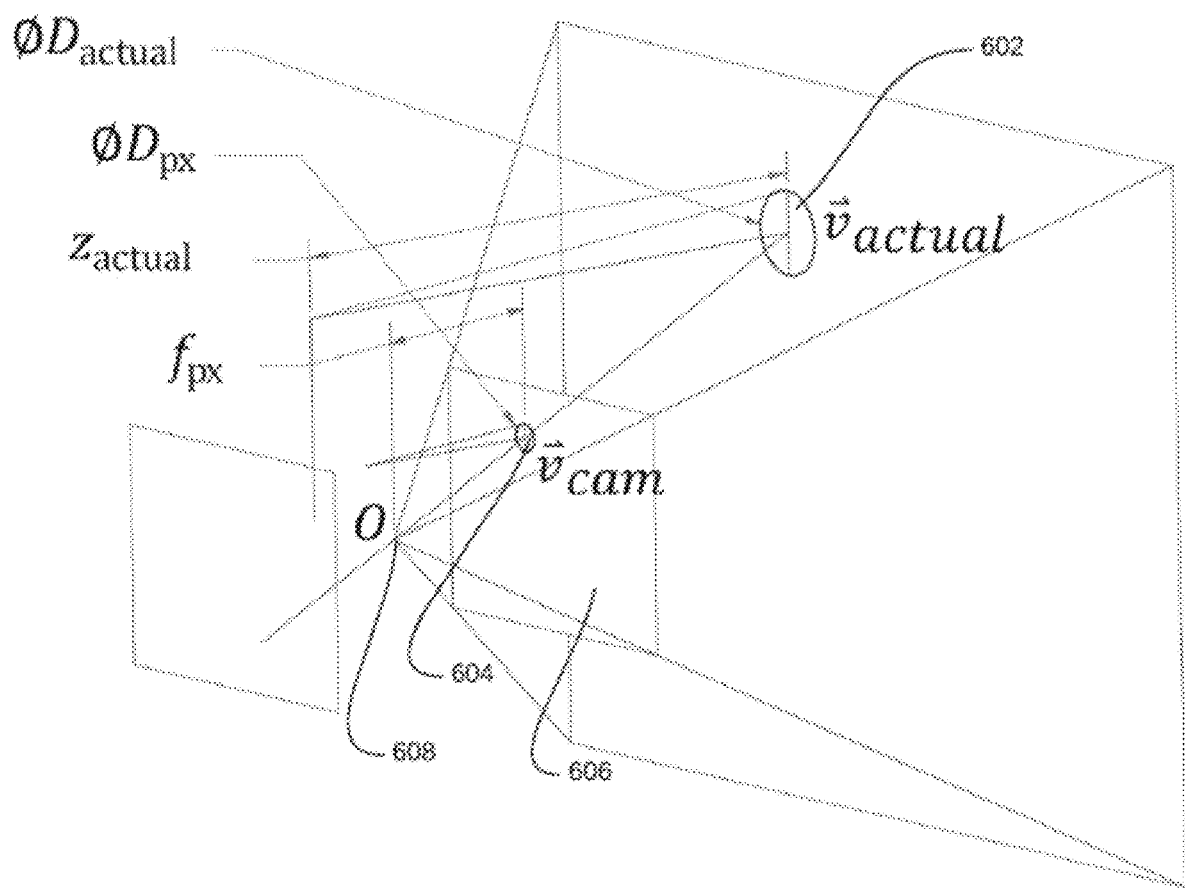
FIG. 6 illustrates a three-dimensional view of a spatial relationship between a camera, a virtual image of the camera, and a fiducial according to various arrangements.

FIG. 6 illustrates a three-dimensional view of a spatial relationship between the camera 332 (FIG. 3), a virtual image of the camera 332, and a fiducial according to various arrangements.

Referring to FIGS. 1A-6, in some arrangements, the image processing circuit 408c is configured to represent locations within an image (e.g., the binary image 500b) as pixel coordinate values (u, v) within the image. In particular arrangements, the top left-hand position of an image is designated as coordinates (0, 0), while the u-coordinate value increases along with movement towards the right-hand side of the image and the v-coordinate value increases along with movement towards the bottom of the image. In other arrangements, any other suitable coordinate system is used to identify locations within an image (e.g., (0, 0) can be located at the bottom right-hand corner of the image, while movement towards the left-hand side increases the u-coordinate value and movement towards the top of the image increases the v-coordinate value, and so on). In some arrangements, the image processing circuit 408c transforms these image coordinates into homogenous camera coordinates using a camera intrinsics matrix and camera distortion coefficients of the camera 332, which are known parameters that can be computed based on a camera calibration procedure of the camera 332.

In some arrangements, to convert the homogenous camera coordinates into physical unit camera coordinates, the image processing circuit 408c is configured to determine a physical unit distance associated with a homogenous camera coordinate vector. For homogeneous coordinates, location points are considered equivalent up to multiplication by a non-zero scalar, as represented by the following equation, in which $\vec{v}_{cam}$ is a vector from an origin of the camera 332 to a location of a fiducial in a virtual camera image, x is a coordinate value along an x-axis of the virtual camera image, y is a coordinate value along a y-axis of the virtual camera image, and a is the non-zero scalar:

$$\vec{v}_{cam} = \begin{bmatrix} x \\ y \\ 1 \end{bmatrix} \approx a \cdot \begin{bmatrix} x \\ y \\ 1 \end{bmatrix} = \begin{bmatrix} ax \\ ay \\ a \end{bmatrix}$$

FIG. 6 shows a real-world fiducial 602, a virtual image fiducial 604 at a virtual camera image 606, and a camera origin 608. In some arrangements, $\vec{v}_{cam}$ represents a vector from the camera origin 608 to the location of the virtual image fiducial 604 and $\vec{v}_{actual}$ represents a vector from the camera origin 608 to the location of the real-world fiducial 602. In some arrangements, $f_{px}$ represents the focal length of the camera 332 (e.g., measured in units of a pixel size of the sensor of the camera 332), which is a known parameter. In further arrangements, $\phi D_{px}$ represents a diameter of the virtual image fiducial 604 (e.g., in pixels) and $\phi D_{actual}$ represents a diameter of the real-world fiducial 602, which are both known parameters. In some arrangements, $z_{actual}$ represents a distance from the camera origin 608 to the real-world fiducial 602.

In some arrangements, the image processing circuit 408c is configured to determine $\vec{v}_{actual}$ based on the above equation and the known parameters. For example, in particular arrangements, the virtual camera image 606 is located at a distance $f_{px}$ from the camera origin 608. Accordingly, in some arrangements, using similar triangles, and knowing $f_{px}$, $\phi D_{px}$, and $\phi D_{actual}$, the image processing circuit 408c is configured to determine $z_{actual}$. In further arrangements, the image processing circuit 408c is configured to multiply $\vec{v}_{cam}$ by a scalar constant such that the z-coordinate component of $\vec{v}_{cam}$ equals $z_{actual}$, which results in $\vec{v}_{actual}$. In other words, for example, by multiplying $\vec{v}_{cam}$ by the scalar constant that results in the z-coordinate component of $\vec{v}_{actual}$ being equal to $z_{actual}$, the x-coordinate and the y-coordinate components of $\vec{v}_{actual}$ are also determined (e.g., as illustrated by the above equation).

As such, in some arrangements, the image processing circuit 408c is configured to utilize the optical parameters of the camera 332 and the known size of the fiducial 602 to determine the location of the fiducial 602 relative to the camera 332. In further arrangements, the image processing circuit 408c is configured to apply boundary limits to ensure that the detected position of the fiducial 602 falls within a reasonable predetermined range of positions relative to the camera 332 for actual use.

In some arrangements, the registration circuit 408d is configured to transform the camera coordinates (e.g., $\vec{v}_{actual}$) obtained by the image processing circuit 408c into robot coordinates for use by the robotics control circuit 408f in controlling the robotics 333 for positioning the probe 331 during operation of the device 330. In particular arrangements, transformations between the camera coordinate system and the robot coordinate system are performed using homogenous coordinates.

In particular arrangements, the registration circuit 408d stores a coordinate transformer class that stores a relationship between camera coordinates and robot coordinates (e.g., a coordinate transformation matrix that is a 4×4 matrix). For example, in some arrangements, positions in camera coordinates are represented as a 3×1 vector (e.g., $\vec{v}_{actual}$), and the registration circuit 408d is configured to convert the 3×1 camera coordinates into a homogenous coordinate representation by appending a $4^{th}$ coordinate having a value of 1 (e.g., [x, y, z] becomes [x, y, z, 1]). In further arrangements, the registration circuit 408d is configured to multiply the homogenous coordinate-represented camera coordinate vector by the stored coordinate transformation matrix to obtain a homogenous robot coordinate vector. In some arrangements, the coordinate transformation matrix that facilitates transformation of camera coordinates into robot coordinates is of the form:

$$\begin{bmatrix} R & t \\ 0 & 1 \end{bmatrix}$$

In particular arrangements, R is a 3×3 rotation matrix for applying a change in orientation between the camera coordinate system and the robot coordinate system, and t is a translation between the origin of the robot coordinate system and the camera coordinate system (e.g., expressed as a 3×1 vector in the robot coordinate system). In some arrangements, the inverse of the coordinate transformation matrix can be utilized to transform the robot coordinates into the camera coordinates. Accordingly, in some arrangements, the registration circuit 408d is configured to utilize the known spatial relationship between the origin of the workspace of the robotics 333 and the origin of the camera 332 to transform locations relative to the camera 332 into locations relative to the robotics 333. In further arrangements, the registration circuit 408d is configured to apply additional boundary limits to ensure that the detected positions of the fiducials fall within a reasonable range of positions relative to the origin of the workspace of the robotics 333 for actual use. In some arrangements, the detected fiducials are displayed to an operator for confirmation that the fiducials are properly detected. For example, one or more of the preprocessed images (e.g., the image 500a) and the binary images (e.g., the image 500b) can be displayed by the output device 404. In some examples, the selected contours corresponding to the fiducials can be superimposed onto a preprocessed image to be displayed to the operator. For example, the fiducials 502a and 502b as shown in FIG. 5A can be displayed in a graphical state that emphasizes the fiducials 502a and 502b by highlighting the fiducials 502a and 502b, adjusting brightness of the fiducials 502a and 502b, and the like, such that the operator can easily see that the contours corresponding to the fiducials 502a and 502b are correctly recognized. The input device 402 may provide a user interactive element (e.g., a soft switch, a button, a dial, or the like) to allow the operator to confirm that the fiducials 502a and 502b are correctly recognized or to reject the selected contours. Responsive to determining that the operator has confirmed the fiducials 502a and 502b via the user interactive element, the controller 408 (e.g., the registration circuit 408d) is configured to transform the camera coordinates into robot coordinates for use by the robotics control circuit 408f in controlling the robotics 333 for positioning the probe 331 during operation of the device 330 in the manner described. Responsive to determining that the operator has rejected the contours via the user interactive element, the fiducial detection method as described herein can be re-run.

In some arrangements, the search parameters circuit 408e is configured to generate a search pattern and path of scanning for the probe 331, including identifying an optimal scanning starting position, during scanning operation of the device 330. The search parameters circuit 408e, in generating the search pattern and path, utilizes the allowable robot workspace determined by the registration circuit 408d, as described above. In particular arrangements, the positions of the detected fiducials are received by the search parameters circuit 408e as reference points to restrict the search area of the probe 331 and to guide the search. In some arrangements, the search parameters circuit 408e instructs the robotics control circuit 408f regarding positioning and travel path of the probe 331 during operation of the device 330 so that the robotics control circuit 408f can send corresponding control signals to the robotics 333 for physically controlling the probe 331.

In summary, in various arrangements, a subject's head having fiducials attached thereto at anatomically relevant locations is received in the headset system and one or more images of the subject's head are captured. Image processing is utilized to detect the fiducials. In some arrangements, the detected fiducials are displayed to an operator for confirming that the detected locations of the fiducials are correct. The locations of the fiducials in camera coordinates are determined in robot coordinates within the robot workspace, and search parameters utilize the positions of the fiducials to restrict travel of the probe (e.g., to avoid certain areas within the robotic workspace) and to select an optimal position within the workspace to begin scanning by the probe.

Accordingly, in various arrangements, systems and methods for registering the headset system described herein allows for registration of a robotic probe with respect to a subject's anatomy (e.g., corner of the eye and tragus). In some arrangements, systems and methods described herein reduce setup time of a headset system in preparation of a scan, while increasing accuracy of scans by repeatable and accurate positioning of a probe by consistently guiding the probe to scan at anatomically relevant positions. In addition, systems and methods described herein increase safety of a headset system by explicitly restricting movement of the headset system with respect to a subject's anatomy (e.g., by preventing the probe from traveling beyond locations anterior from the corner of the eye).

In additional arrangements, systems and methods of registering a headset system can determine from where a signal scanned by a probe is originating from based on a current position of the probe in robot coordinates within the robotic workspace. For example, based on the current position of the probe, the system can determine that the probe is capturing signals originating from the middle cerebral artery (MCA) of the brain.

According to other arrangements, instead of capturing images of fiducials positioned on a subject's head and processing the images, as described above, other systems and methods of registering a subject's head within a headset system can be used. As an example, in some arrangements, a distance from a camera can be established as a predetermined value (e.g., as if imaging a flat surface at a known distance). For example, the distance from the camera can be input by an operator. As such, the operator can simply select one or more points on an image captured by the camera, and the system can determine robot coordinates of each of the one or more coordinates based on the predetermined distance from the camera.

In other arrangements, systems and methods of registering a subject's head within a headset system implement machine vision to automatically detect locations of anatomically significant landmarks of a subject's head (e.g., the corner of the eye and the tragus). For example, the machine vision can utilize machine learning techniques to analyze various images of subject heads to train the system in identifying the anatomically significant landmarks. Training sets including images and corresponding results (e.g., identified landmarks) as determined by a human operator can be used to train the artificial intelligence (e.g., the AI) to identify anatomically significant landmarks. The controller 408 can be used to implement a classifier that accepts images of body parts of the subject and outputs identified anatomically significant landmarks. In yet other arrangements, systems include a plurality of cameras (e.g., two) at a single side of the headset system such that stereo vision is implemented in determining distances of locations at a head of a subject (e.g., by taking an image of a single point by two different and physically separate cameras). In particular arrangements, a positioning stage attached to a single camera can be utilized for taking multiple images of a point to implement stereo vision (e.g., the single camera takes a first image, the positioning stage moves the camera, and the same camera takes a second image). In some arrangements, instead of using the positioning stage, the single camera is attached to the robotics of the scanning device such that the camera can be moved around for implementing stereo vision (e.g., along with the probe).

Figure 7:
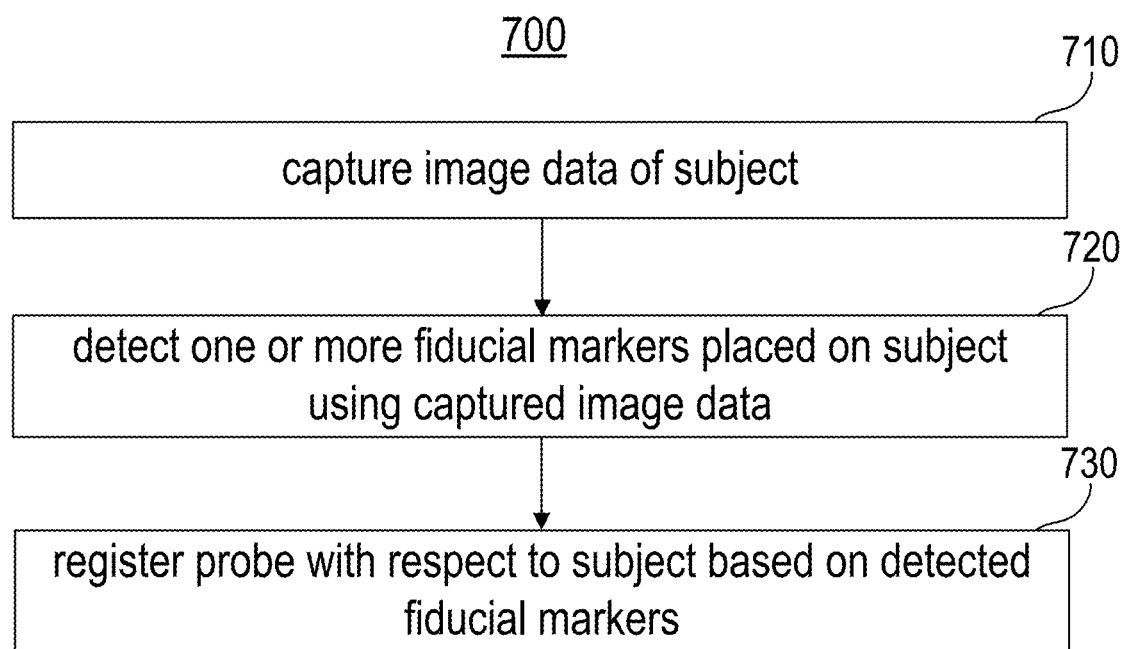
FIG. 7 is a flowchart diagram illustrating an example method for registering a probe of a headset system with respect to a subject according to various arrangements.

FIG. 7 is a flowchart diagram illustrating an example method 700 for registering a probe (e.g., the probe 131 of FIGS. 1A and 2B and/or the probe 331 of FIGS. 3A-4) of a headset system (e.g., the headset system 100 of FIG. 1 and/or the headset registration system 400 of FIG. 4) with respect to a subject according to various arrangements. Referring to FIGS. 1A-7, at 710, image data (e.g., one or more images) of a subject is captured by one or more cameras (e.g., the camera 332) in the manner described. At 720, the controller 408 is configured to detect one or more fiducial markers (e.g., the fiducials 502a and 502b) placed on the subject using the captured image data in the manner described. At 730, the controller 408 is configured to register the probe with respect to the subject based on the detected fiducial markers in the manner described. While a lateral side of the subject is described as a body part of interest for the method 700 (e.g., the camera 332 captures images of the lateral side of the subject at 710, and the images are analyzed for registration in the manner described with respect to 720 and 730), the method 700 can be implemented with respect to any suitable body part of the subject. For example, the camera 332 can be positioned at and/or moved relative to any suitable body part, such that the images of that body part can be captured by the camera 332 and analyzed in the manner described herein.

Figure 8:
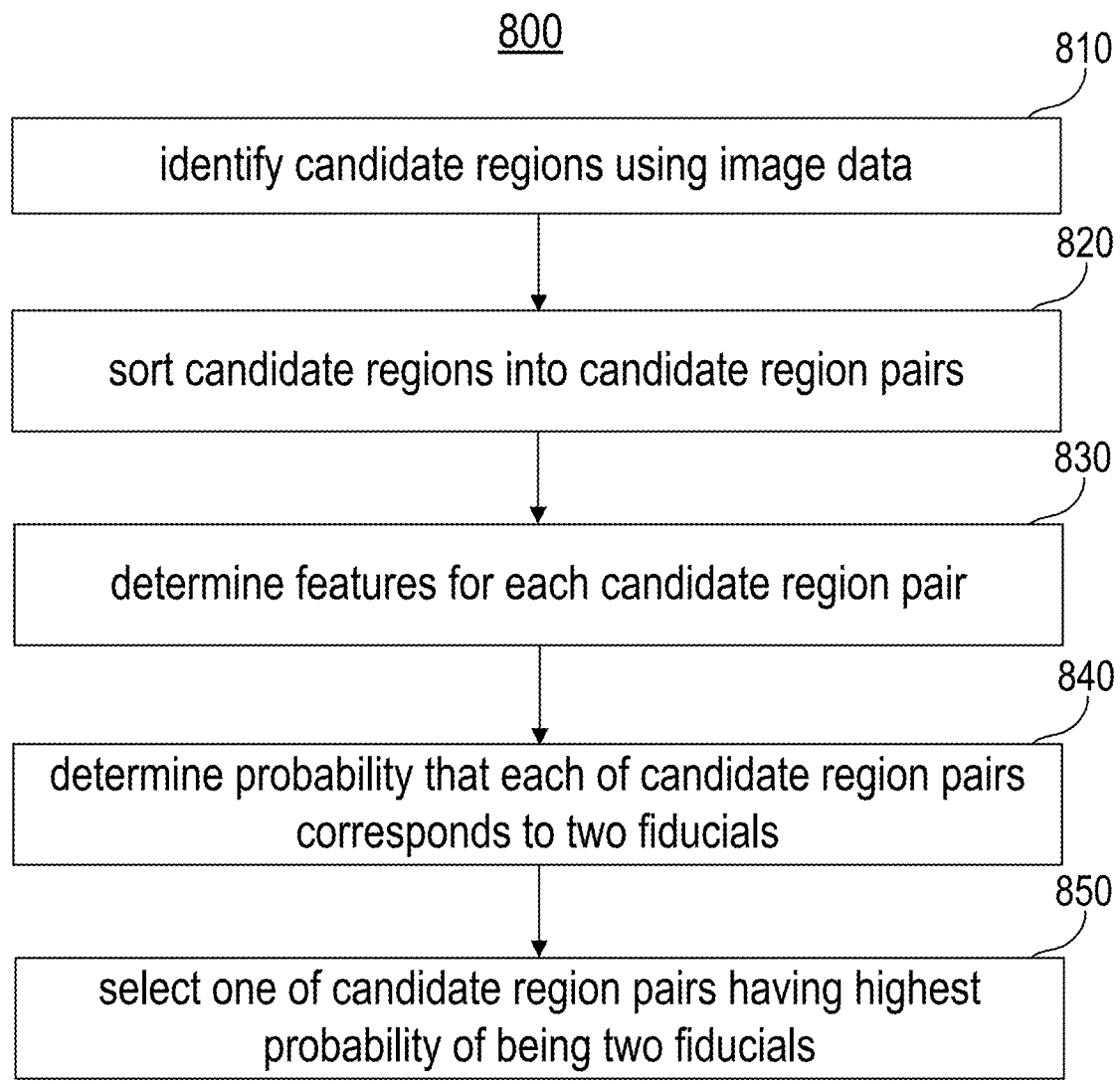
FIG. 8 is a flowchart diagram illustrating an example method for determining a fiducial pair according to various arrangements.

FIG. 8 is a flowchart diagram illustrating an example method 800 for determining a fiducial pair (e.g., the fiducials 502a and 502b) according to various arrangements. Referring to FIGS. 1A-8, the method 800 is an example method by which a pair of fiducials (e.g., the fiducials 502a and 502b) can be detected at block 720, assuming that a pair of fiducials are placed on a lateral side of a head of a subject.

At 810, the controller 408 (e.g., the image processing circuit 408c) is configured to identify candidate regions. In some examples involving machine vision, candidate regions (e.g., candidate elliptic regions) $c_1, c_2, \ldots, c_n$ can be identified using Maximally Stable Extremal Regions (MSER) algorithm, which accepts as inputs two images of a given lateral side of the subject's head that are from different viewpoints. An MSER algorithm can be used to detect elliptic regions in images. As described, a single camera can be moved to take two images of a given lateral side of the subject's head from different viewpoints. Alternatively, two cameras at different positions (different viewpoints) can each take an image of the lateral side of the subject's head.

In some examples, each candidate region can be represented by a list of pixels that make up the respective candidate region. In some examples, each candidate region can be approximated by an ellipse obtained through suitable fitting algorithms. Some of the candidate regions corresponding to fiducials. Other candidate regions correspond to artifacts created by backgrounds of the images or light reflections on the subject's face.

At 820, the controller 408 (e.g., the image processing circuit 408c) is configured to sort the identified candidate regions into candidate region pairs, each candidate region pair includes two candidate regions. For example, all permutations of pairings of the candidate regions can be determined.

At 830, the controller 408 (e.g., the image processing circuit 408c) is configured to determine features for candidate region pair. The features can be a feature of each individual candidate region in the pair, or a relative feature indicative of a relative property of the pair. In some arrangements, each candidate region (e.g., each candidate elliptic region) can be characterized with one or more of location, size, shape (eccentricity), image intensity, and local texture. Location refers to a location of a fiducial in the images 500a and/or 500b as represented with the pixel coordinate values (u, v) described herein. Size refers to a total area of an ellipse fitted to a candidate region. Eccentricity refers to a ratio between lengths of two axes of an ellipse fitted to a candidate region. Intensity refers to an intensity distribution within a candidate region determined using an average value in some examples, and in alternative examples, the intensity distribution within the candidate region can be determined by using a histogram. In constructing the histogram, all have the same limits (e.g., minimum and maximum values) and that normalization is applied to pixels inside of the candidate region. A histogram for each candidate region in the image is generated, where all of those histograms have the same limits. In some examples, intensity surrounding an ellipse corresponding to a candidate region can be described using an average value or a histogram in the manner described. An outer region that surrounds the ellipse can be defined by an elliptic ring based on the outer boundary of the inner ellipse and its copy scaled by 175%. That is, in addition to the intensity inside the ellipse, the intensity of an elliptical annulus or ring of an inner major axis and a minor axis equal to the major axis and minor axis of the elliptical region, respectively. An outer major axis and a minor axis equal to 175% of the major and minor axes of the elliptical region, respectively. In some examples, an ideal shape of a fiducial is a perfect circle. Given the viewpoint of the camera and the position/orientation of the subject's head, the perfect circle may appear as an ellipsoid shape in the images 500a and/or 500b. A shape descriptor (e.g., a general shape descriptor, a shape context descriptor, or the like) can be used to capture how close the candidate region is from an ellipsoid shape. Local texture refers to an appearance of a candidate region as represented using a texture descriptor. In some examples, an image gradient is extracted within an ellipse corresponding to the candidate region, where the image gradient can be summarized as a histogram, for example, using a suitable technique such as but not limited to, Speeded Up Robust Features (SURF).

In the examples in which two fiducials (e.g., the fiducials 502a and 502b) are placed on the head of the patient, two fiducials can be assumed to be present in any images captured by the camera (if the camera is properly position). Features indicative of the relationship between two candidate regions can be used to determine whether a pair of candidate regions can be the two fiducials. For example, spatial relation between two candidate regions or two ellipses corresponding thereof can be used to distinguish the fiducials from artifacts. Relative position refers to a distance and a slope between the two candidate regions.

At 840, the controller 408 (e.g., the image processing circuit 408c) is configured to determine a probability that each of the candidate region pairs corresponds to the fiducials placed on the subject. At 850, the controller 408 (e.g., the image processing circuit 408c) is configured to select the candidate region pair having the highest probability of being the fiducials.

A probabilistic framework can be established to select a pair of the candidate regions as fiducials based on the features such as but not limited to, one or more of a location, size, shape, image intensity, local texture, and spatial relationship. For example, the features can be described in a feature vector with respect to each pair of candidate regions ($c_i$, $c_j$), such as but not limited to, in the form $F_{i,j} \leftarrow$[features$_i$, features$_j$, and features$_{i,j}$]. The term features$_{i,j}$ refers to relative features such as but not limited to, the spatial relationship (in terms of distance and/or slope) between two candidate regions. The term features$_i$ refers to features (e.g., one or more of the location, size, shape, image intensity, and local texture) of a first candidate region of the candidate region pair. The term features$_j$ refers to features (e.g., one or more of the location, size, shape, image intensity, and local texture) of a second candidate region of the candidate region pair.

The weights for each of the features (location, size, shape, image intensity, local texture, and spatial relationship) can be determined using machine learning. For example, manually label training set (e.g., data examples) can be provided to allow the image processing circuit 408c (implementing AI) to learn weights assigned to each of the features. A probabilistic mapping for each individual feature can be determined based on machine learning. A value of each feature is mapped by a probabilistic model to output a value that represents how likely the feature belongs to a fiducial in terms of a probability. Then, the probability of all features (individual and relative features) are combined, for example, using a regression model to determine a final predicted score for each pair of candidate regions. The pair with the highest score is selected.

In some arrangements, an example of a probabilistic model for each given feature can be a Gaussian distribution model in which mean μ and standard deviation σ are estimated from the data examples of actual fiducials:

$$g(x) = \frac{1}{\sigma\sqrt{2\pi}} e^{-\frac{1}{2}\left(\frac{x-\mu}{\sigma}\right)^2}$$

In other words, the data examples in the training set can be used to determine μ and σ. For instance, μ and σ are the mean of that feature in the training set and the standard deviation in the training set.

In other examples, instead of a Gaussian distribution model, Kernel Density Estimation (KDE) can be used as a probabilistic model for each given feature.

In some examples, the overall probability for a candidate region pair can be determined by combining (e.g., multiplying) the probability for each feature (individual or relative).

In some examples, all features may not contribute equally to correct prediction. Thus, the features can be weighted, for example, using regression techniques. In one example, a ridge regression model can be implemented, where the weights are estimated from examples of labeled regions of actual physically tested examples and from the training data set. In other examples, kernel ridge regression can be used instead of the ridge regression.

While the methods 700 and 800 are described with reference to images (e.g., the images 500a and 500b) of lateral sides of a subject's head, the methods 700 and 800 can be implemented with respect to other body parts of the subject such as but not limited to, a front side of the face of the subject (e.g., to obtain ultrasound signals of the head of the subject), chest (e.g., to obtain ultrasound signals of the heart), torso (e.g., to obtain ultrasound signals of various organs), limbs (e.g., to obtain ultrasound signals of blood flow in the limbs), and so on.

While fiducials (e.g., the fiducials 502a and 502b) are described to be used to facilitate identification of anatomic features of the subject, the anatomic features can be identified without using any fiducials. For example, the camera 332 may capture images of body parts of the subject (without any fiducials attached thereto). The controller 408 (e.g., the image processing circuit 408c) can process the captured images using suitable image processing and image recognition techniques (e.g., machine vision) to identify objects captured in the images as body parts of anatomical features of interest.

In other arrangements, any other suitable technique or device for locating and detecting distances of areas of a subject's head from a scanning device can be implemented during the registration process, such as, but not limited to, structured light, time of flight cameras, time of flight sensors, infrared sensors, and so on. For example, in some arrangements, a thermal camera is utilized to take an infrared image of the subject's head such that direct visualization of the subject's suitable scanning area (e.g., temporal window) is obtained.

In some arrangements, the systems 100 and 400 as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the systems 100 and 400 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

What is claimed is:

1. A method for operating a transducer of a headset system that collects ultrasound data from a subject, the method comprising:
   detecting at least one fiducial marker placed on the subject using image data, the image data comprising two images of the subject from different viewpoints; and
   determining a scanning area of the subject bounded by the at least one fiducial marker; and
   restricting the transducer from traveling beyond the scanning area while the transducer collects the ultrasound data.

2. The method of claim 1, further comprising determining a plurality of candidate regions using the image data based on machine vision.

3. The method of claim 2, wherein the plurality of candidate regions are identified using the image data based on a Maximally Stable Extremal Regions (MSER) algorithm.

4. The method of claim 2, wherein each of the plurality of candidate regions comprises a list of pixels.

5. The method of claim 2, further comprising
   sorting the plurality of candidate regions into candidate region pairs;
   determining features for each of the candidate region pairs;
   determining a probability that each of the candidate region pairs corresponds to the at least one fiducial marker; and
   selecting two or more candidate regions based on the probability.

6. The method of claim 5, wherein sorting the plurality of candidate regions into the candidate region pairs comprises determining permutations of pairings of the plurality of candidate regions.

7. The method of claim 5, wherein each of the features comprise one or more of a location, a size, a shape, an image intensity, or a local texture.

8. The method of claim 7, wherein the probability that each of the candidate region pairs corresponds to the at least one fiducial marker is determined based on the one or more of the location, the size, the shape, the image intensity, or the local texture.

9. The method of claim 5, wherein the probability that each of the candidate region pairs corresponds to the at least one fiducial marker is determined based on a weight assigned to each of the features.

10. A non-transitory computer-readable medium having computer-readable instructions, such that when executed, causes a processor of a headset system to operate a transducer of the headset system that collects ultrasound data from a subject by:
    detecting at least one fiducial marker placed on the subject using image data, the image data comprising two images of the subject from different viewpoints; and
    determining a scanning area of the subject bounded by the at least one fiducial marker; and
    restricting the transducer from traveling beyond the scanning area while the transducer collects the ultrasound data.

11. The non-transitory computer-readable medium of claim 10, wherein the processor is further caused to determine a plurality of candidate regions using the image data based on machine vision.

12. The non-transitory computer-readable medium of claim 11, wherein the plurality of candidate regions are identified using the image data based on a Maximally Stable Extremal Regions (MSER) algorithm.

13. The non-transitory computer-readable medium of claim 11, wherein each of the plurality of candidate regions comprises a list of pixels.

14. The non-transitory computer-readable medium of claim 11, the processor is further caused to:
    sort the plurality of candidate regions into candidate region pairs;
    determine features for each of the candidate region pairs;
    determine a probability that each of the candidate region pairs corresponds to the at least one fiducial marker; and
    select two or more candidate regions based on the probability.

15. The non-transitory computer-readable medium of claim 14, wherein sorting the plurality of candidate regions into the candidate region pairs comprises determining permutations of pairings of the plurality of candidate regions.

16. The non-transitory computer-readable medium of claim 14, wherein each of the features comprise one or more of a location, a size, a shape, an image intensity, or a local texture.

17. The non-transitory computer-readable medium of claim 16, wherein the probability that each of the candidate region pairs corresponds to the at least one fiducial marker is determined based on the one or more of the location, the size, the shape, the image intensity, or the local texture.

18. The non-transitory computer-readable medium of claim 15, wherein the probability that each of the candidate region pairs corresponds to the at least one fiducial marker is determined based on a weight assigned to each of the features.

19. A system, comprising:
a controller configured to:
  detect at least one fiducial marker placed on the subject using image data, the image data comprising two images of the subject from different viewpoints; and
  determine a scanning area of the subject bounded by the at least one fiducial marker; and
  restrict the transducer from traveling beyond the scanning area while the transducer collects the ultrasound data.

20. The system of claim 19, wherein the processor is further caused to determine a plurality of candidate regions using the image data based on machine vision.

* * * * *